United States Patent [19]
Alexandru

[11] Patent Number: 6,089,096
[45] Date of Patent: Jul. 18, 2000

[54] ELEVATION FOCUSING BY BEAMFORMER CHANNEL SHARING

[75] Inventor: Radu Alexandru, Cheshire, Conn.

[73] Assignee: Aloka Co., Ltd., Tokyo, Japan

[21] Appl. No.: 09/108,678

[22] Filed: Jul. 1, 1998

[51] Int. Cl.[7] .................................................. G01N 29/00
[52] U.S. Cl. ............................................. 73/626; 73/625
[58] Field of Search ............................ 73/618, 625, 626, 73/627, 628

[56] References Cited

U.S. PATENT DOCUMENTS

| | | |
|---|---|---|
| 5,186,175 | 2/1993 | Hirama et al. . |
| 5,301,168 | 4/1994 | Miller . |
| 5,349,262 | 9/1994 | Grenon et al. . |
| 5,492,134 | 2/1996 | Souquet . |
| 5,677,491 | 10/1997 | Ishrak et al. . |
| 5,787,049 | 7/1998 | Bates ............................................. 367/7 |
| 5,846,201 | 12/1998 | Adams .................................... 600/447 |

OTHER PUBLICATIONS

Wildes et al, "Elevation Performance of 1.25D and 1.5D Transducer Arrays", IEEE Transactions On Ultrasonics, Ferroelectrics, And Frequency Control vol. 44, No. 5, Sep. 1997.

Turnball et al, "Simulation of B–Scan Images From Two–Dimensional Transducer Arrays: Part II—Comparisons Between Linear And Two–Dimensional Phased Arrays", Ultrasonic Imaging, 14, 344–353 (1992).

Primary Examiner—Richard A. Moller
Attorney, Agent, or Firm—Cantor Colburn LLP

[57] ABSTRACT

An ultrasound imaging system provides for depth-variable elevational and azimuthal focusing by combining electronic beamforming and fixed mechanical lens (or element shaping). The imaging system includes a plurality of beamformer channels that are selectively allocated to the imaging elements of an array. For phased arrays, a switching circuit controls the allocation of the beamformers, while a linear/convex array also requires an aperture shifting circuit for shifting the aperture along the array. The elevational focusing is achieved using a small number of beamformer channels by sharing the beamformer channels assigned to azimuthal elements for far field imaging and to elevational elements for near field imaging. A portion of the beamformer channels are connected to elevational elements (elements in the off-center rows) during near-field imaging. During far-field imaging, these channels connected to the elevational elements are allocated to the lateral elements for azimuthal focusing, and the elevational elements are allocated directly to the center-row elements of their column. The mechanical focus depth is chosen to be in the far field to provide improved elevation focusing in the far field without the need for electronic beamforming delays. In addition, since the f-number is large in the far field, the depth of focus will be large.

61 Claims, 17 Drawing Sheets

| K=0 | 1 | 2 | 3 | 4 | 5 | 6 | 7 | 8 | 9 | 10 | 11 |
|---|---|---|---|---|---|---|---|---|---|---|---|
|  |  |  |  | 11 | 10 | 1 | 0 |  |  |  |  |
|  |  |  |  | 9 | 8 | 3 | 2 |  |  |  |  |
|  |  |  |  | 4 | 5 | 6 | 7 |  |  |  |  |
|  |  |  |  | 9 | 8 | 3 | 2 |  |  |  |  |
|  |  |  |  | 11 | 10 | 1 | 0 |  |  |  |  |

Rows r = 2, 1, 0, 1, 2; Columns (M); m spans columns 4–7; Rows (N)

FIG. 9

| K=0 | 1 | 2 | 3 | 4 | 5 | 6 | 7 | 8 | 9 | 10 | 11 |
|---|---|---|---|---|---|---|---|---|---|---|---|
|  |  |  |  | 1 | 0 | 10 | 11 |  |  |  |  |
|  |  |  |  | 3 | 2 | 9 | 8 |  |  |  |  |
|  |  |  |  | 4 | 5 | 6 | 7 |  |  |  |  |
|  |  |  |  | 3 | 2 | 9 | 8 |  |  |  |  |
|  |  |  |  | 1 | 0 | 11 | 10 |  |  |  |  |

FIG. 10

| K=0 | 1 | 2 | 3 | 4 | 5 | 6 | 7 | 8 | 9 | 10 | 11 |
|---|---|---|---|---|---|---|---|---|---|---|---|
|  |  |  |  | 0 | 1 | 10 | 11 |  |  |  |  |
|  |  |  |  | 2 | 3 | 8 | 9 |  |  |  |  |
|  |  |  |  | 4 | 5 | 6 | 7 |  |  |  |  |
|  |  |  |  | 2 | 3 | 8 | 9 |  |  |  |  |
|  |  |  |  | 0 | 1 | 10 | 11 |  |  |  |  |

FIG. 17A

| K=8 | 9 | 10 | 11 | 0 | 1 | 2 | 3 | 4 | 5 | 6 | 7 |
|---|---|---|---|---|---|---|---|---|---|---|---|
| A=0 | 1 | 2 | 3 | 4 | 5 | 6 | 7 | 8 | 9 | 10 | 11 |
|  |  |  |  |  |  |  |  | 2 | 3 | 4 | 5 |
|  |  |  |  |  |  |  |  | 0 | 1 | 6 | 7 |
|  |  |  |  |  |  |  |  | 8 | 9 | 10 | 11 |
|  |  |  |  |  |  |  |  | 0 | 1 | 6 | 7 |
|  |  |  |  |  |  |  |  | 2 | 3 | 4 | 5 |

FIG. 17B

| K=8 | 9 | 10 | 11 | 0 | 1 | 2 | 3 | 4 | 5 | 6 | 7 |
|---|---|---|---|---|---|---|---|---|---|---|---|
| A=0 | 1 | 2 | 3 | 4 | 5 | 6 | 7 | 8 | 9 | 10 | 11 |
|  |  |  |  |  |  |  |  | 2 | 3 | 4 | 5 |
| 0 | 1 |  |  |  |  | 6 | 7 | 8 | 9 | 10 | 11 |
| 0 | 1 |  |  |  |  | 6 | 7 | 8 | 9 | 10 | 11 |
| 0 | 1 |  |  |  |  | 6 | 7 | 8 | 9 | 10 | 11 |
|  |  |  |  |  |  |  |  | 2 | 3 | 4 | 5 |

FIG. 17C

| K=8 | 9 | 10 | 11 | 0 | 1 | 2 | 3 | 4 | 5 | 6 | 7 |
|---|---|---|---|---|---|---|---|---|---|---|---|
| A=0 | 1 | 2 | 3 | 4 | 5 | 6 | 7 | 8 | 9 | 10 | 11 |
| 0 | 1 | 2 | 3 | 4 | 5 | 6 | 7 | 8 | 9 | 10 | 11 |
| 0 | 1 | 2 | 3 | 4 | 5 | 6 | 7 | 8 | 9 | 10 | 11 |
| 0 | 1 | 2 | 3 | 4 | 5 | 6 | 7 | 8 | 9 | 10 | 11 |
| 0 | 1 | 2 | 3 | 4 | 5 | 6 | 7 | 8 | 9 | 10 | 11 |
| 0 | 1 | 2 | 3 | 4 | 5 | 6 | 7 | 8 | 9 | 10 | 11 |

ELEVATION FOCUSING BY BEAMFORMER CHANNEL SHARING

FIELD OF THE INVENTION

The present invention relates to the field of ultrasonic imaging as used for example in medical diagnostic scanning. More particularly, the invention relates to systems and methods of forming ultrasound beams which are focused both in the azimuth and in the elevation directions at all depths of the imaging field.

BACKGROUND OF INVENTION

Ultrasound imaging systems for medical diagnostics scan a subject with ultrasound beams in a sector or rectangular pattern. A transducer emits and focuses the beams along certain linear directions or scan lines. The emitted beam reflects back, in the form of an echo, acoustic discontinuities to the transducer along the same scan lines. The received beam is converted to electrical signals which generate an image on a two-dimensional display representative of a planar cross-section through the subject. The resolution of an ultrasound scanner depends on how well the beams are locally focused along the scan lines.

The transducers of modem ultrasound imaging systems consist of arrays of small rectangular piezoelectric elements to form the focused ultrasound beams. The active transducer area of the portion of the transducer surface which emits and/or receives the sound waves is referred to as the "aperture". The transmit and receive apertures are not necessarily identical.

It is important to focus the beams both in the scanning plane (azimuthal direction) and in the orthogonal (elevational direction or "out of the image plane") plane to provide a well-defined image of the subject. Focusing of the beam at a certain point in the medium is achieved by delaying the waves emitted from or received at various points in the aperture. By pulsing the aperture's elements with predetermined delays relative to a reference "start" time, the transmitted acoustic waves arrive in phase at the focal point in the medium, interacting constructively, to form beams focused along the desired scan lines. Likewise, by delaying the received echoes such that the echoes from each point along the scan lines are in phase, and then adding the delayed echoes, a signal representing mostly the echoes from points along the desired scan line is formed. As a result, the echoes from points away from the scan line arrive with different delays and tend to cancel each other in the summation. The process of forming the focused beams is called beamforming, and therefore, the devices performing this function are called respectively transmit and receive beamformers.

The ratio of the focal depth, defined as the distance from the center of the aperture to the focal point, to the linear dimension of the aperture in a certain direction (e.g., azimuthal or elevational) is called the "f-number". The azimuthal and the elevational "f-numbers" are generally different. The smaller the "f-number" at a certain focal depth, the better the beam focusing at that depth. For a fixed set of delays corresponding to a certain focal depth, the larger the "f-number", the larger the depth of focus, which is defined as the depth range over which the beam stays focused.

Transducers in which the whole array defines a single aperture to generate all beams are called "phased arrays". Transducers in which the aperture is a subset of the whole array, and the aperture's position on the array is shifted in order to generate different beams, are called "linear" or "curvilinear" arrays.

In most current systems the transducer array consists of one row of rectangular elements arranged sequentially along a straight or curved line lying in the image plane. This arrangement is called an 1D array. Each element in the aperture is connected to a transmit beamformer channel and a receive beamformer channel. By appropriately controlling the beamforming delays, the 1D array may be focused in the azimuthal direction at any desired depth. Focusing in the elevational direction is achieved by means of a mechanical lens or by appropriately shaping the elements along the elevational direction. The elevation focal depth, therefore, is fixed. This is a limitation of the current technology, requiring the use of multiple probes, one for each desired elevation focal depth.

In order to extend the depth range over which elevation focus is achieved, arrays are typically designed with relatively large elevational f-number (low element height). This has the disadvantages of weak elevation focusing and reduced aperture area, resulting in decreased sensitivity.

Variable elevation focal depth can be achieved by constructing two-dimensional arrays (2D arrays) of small square elements and connecting them to independent beamformer channels, thus providing electronic focusing in both the azimuthal and elevational directions. This method, however, requires a number of beamformer channels that is prohibitively expensive. For example, if the array had 128 element columns (in the azimuthal direction) and 64 rows (in the elevation direction), and the symmetrical rows were connected together in pairs, 128*32=4096 channels would be needed. Modem high-end imaging systems typically have 128 beamformer channels, and only a few commercial imaging systems are known to have on the order of 200 beamformer channels.

It has been shown that if only focusing, not steering, needs to be achieved in the elevational direction, then the elevational size of the elements may be substantially increased relative to their azimuthal size. This allows a certain aperture height to be obtained with fewer elements, thus reducing the necessary number of channels. Arrays with multiple rows having much fewer rows than columns are referred to as 1.5D arrays. An article published in Ultrasonic Imaging (Vol. 14, pp. 344–353) show that as few as 3 rows of elements provide some elevation focus enhancement, and 7 rows provide most of the enhancement needed. However, the addition of 4 rows leads to a substantial increase (at least doubling) in the number of beamformer channels.

Other embodiments enhance the elevation focusing without applying additional beamforming delays, by using various combinations of depth-variable element height, apodization, multifocus lenses or multifocus element shaping (e.g., U.S. Pat. Nos. 5,349,262 to Grenon and Vogel; 5,492,134 to Souquet; and 5,677,491 to Ishrak et al.). These methods avoid increasing the number of beamformer channels, but achieve a limited enhancement of the elevation focus over depth. In some cases, these methods sacrifice sensitivity by not using some of the center portion of the receive aperture.

Yet another method, known as "synthetic aperture", shown in U.S. Pat. No. 5,186,175 to Hirama et al shares the beamformer channels between rows of transducers, focusing the rows one at a time, storing the signals representing the partially focused beam, and then combining them to obtain the fully focused beam. This method suffers from a reduced frame rate, susceptibility to motion artifacts, and need for additional hardware for storing and processing the partial beam signals.

SUMMARY OF THE INVENTION

This invention offers advantages and alternatives over the prior art by providing an ultrasound imaging system that includes depth-variable elevational focusing using a combination of electronic beamforming and fixed mechanical lens (or element shaping). The elevational focusing is accomplished using a number of beamformer channels less than the number of elements of the aperture of the array by sharing beamformer channels between azimuthal and elevational elements (elements in the off-center rows). For near-field imaging, the useful azimuthal aperture is typically smaller than the maximum available aperture due to spatial sampling and element directivity considerations, and therefore the beamformer channels are allocated to the elevational elements. For far-field imaging, these channels are allocated to the lateral elements for azimuthal focusing, and the elevational elements are allocated directly to the center-row elements of their column and to the respective beamformer channels for azimuthal focusing. The far-field elevation focusing is provided by a lens or by the shape of the elements.

In accordance with the present invention, an imaging system for focusing ultrasound beams in elevational and azimuthal planes includes an array having a plurality of rows of imaging elements in an elevational plane and a plurality of columns of imaging elements in an azimuthal plane. The elements are interconnected to a plurality of beamformer channels to form the ultrasound beams. A switching circuit, which includes a plurality of switches, preferably allocates a plurality of beamformer channels to elevational elements of a first aperture having a predetermined number of columns and rows for scanning a first depth of an imaging field. For scanning a second depth of the imaging field, the switching circuit further reallocates the beamformer channels allocated to the elevational elements, to azimuthal elements of a plurality of columns added to the first aperture to form a second aperture. A controller provides a control signal to actuate the switches of the switching circuit to allocate the beamformer channels between the elevational element and the azimuthal element of the array.

In accordance with another embodiment of the present invention, a method for focusing ultrasound beams for an array having a plurality of rows of imaging elements in an elevational plane and a plurality of columns of imaging elements in an azimuthal plane includes allocating each of a plurality of beamformer channels to azimuthal and elevational elements defining a first aperture having a predetermined number of rows and columns of elements for scanning a first depth of an imaging field. An ultrasound beam is then focused in the elevation and azimuthal planes at the first depth of the imaging field. For scanning a second depth of the imaging field, at least one element of a column is added to the first aperture to form a second aperture by reallocating at least one beamformer channel of an elevational element of the first aperture to the at least one element of the added column. An ultrasound beam is then focused in the elevational planes and azimuthal plane at the second depth of the imaging field.

BRIEF DESCRIPTION OF DRAWINGS

Referring now to the drawings wherein like elements are numbered alike in the several FIGURES:

FIG. 6A shows active elements of the array of FIG. 1 for imaging Zone 1 and beamformer channels allocated to each active imaging element in accordance with a first allocation method;

FIG. 6B shows active elements of the array of FIG. 1 for imaging Zone 2 and beamformer channels allocated to each active imaging element in accordance with the first allocation method;

FIG. 6C shows active elements of the array of FIG. 1 for imaging Zone 3 and beamformer channels allocated to each active imaging element in accordance with the first allocation method;

FIG. 8 shows active elements of the array of FIG. 1 for imaging Zone 1 and beamformer channels allocated to each active imaging element in accordance with the second allocation method;

FIG. 9 shows active elements of the array of FIG. 1 for imaging Zone 1 and beamformer channels allocated to each active imaging element in accordance with the third allocation method;

FIG. 10 shows active elements of the array of FIG. 1 for imaging Zone 1 and beamformer channels allocated to each active imaging element in accordance with the fourth allocation method;

FIG. 17A–C show a schematic view of the first allocation method for shifting and switching the allocation of the beamformer channels between the imaging elements for Zone 1–3, respectively;

DETAILED DESCRIPTION OF THE INVENTION

Figure 1:
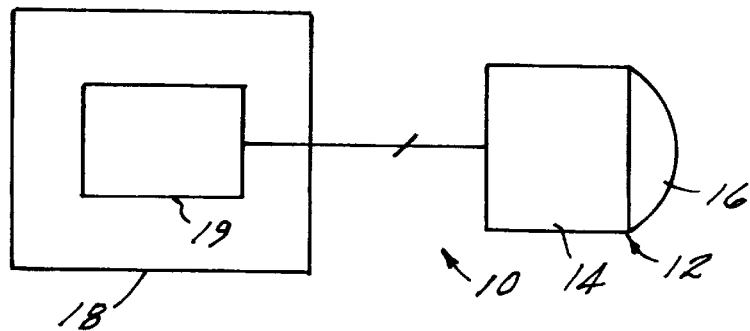
FIG. 1 shows a block diagram of an ultrasound imaging system embodying the present invention.
Figure 2:
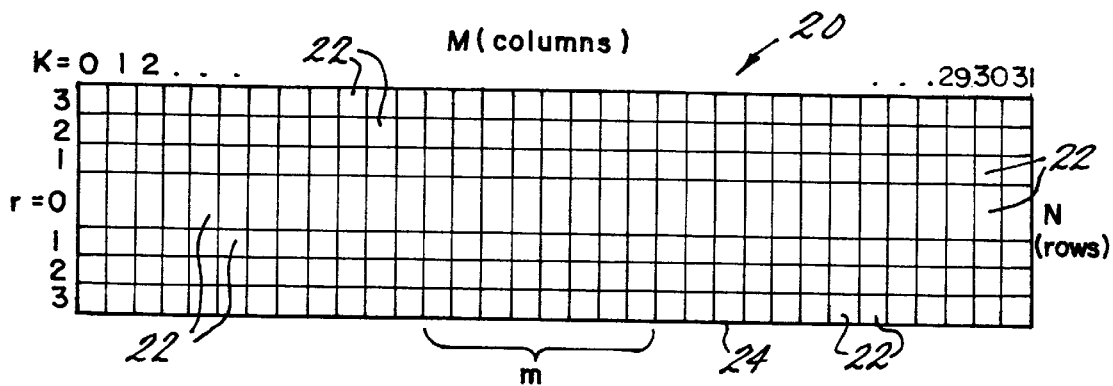
FIG. 2 shows a schematic representation of a transducer of an ultrasound imaging system of an embodiment of the present invention.

In FIG. 1, there is shown an ultrasound imaging system, generally designated 10, for generating images of a subject for medical diagnostics. The imaging system 10 includes a probe head 12 having a transducer 14 and a fixed mechanical lens 16. A scanner 18 provides and receives signals from the transducer which transmits and receives acoustic waves to and from the subject (not shown). The transducer 14 comprises an array 20, preferably a 1.5 array, as shown in FIG. 2, that comprises a plurality of imaging elements 22. Each element 22 is formed of a piezoelectric element that generates an acoustic signal in response to an electric signal or generate an electrical signal in response to a acoustic vibration.

For illustrative purposes the array 20 shown in FIG. 2 is a phased array, and therefore, as described hereinbefore, the entire array comprises the maximum aperture 24. In other words, the number of columns (M) of the maximum aperture is equal to the number of columns (C) of the phased array 20. For a linear or convex array, the number of columns (M) of the maximum aperture 24 is a subset of the total number of columns (C) of the entire array 20. The columns are numbered (k) wherein k=0 to (M−1). The rows are numbered (r), wherein r=0 to 3.

Typically, the maximum aperture 24 includes 128 (azimuthal) columns and 7 (elevational) rows, however, the phased array 20 of FIG. 2 shows a smaller aperture of this type having thirty-two (32) columns and seven (7) rows of imaging elements. The rows (N) and columns (M) of the maximum aperture 24 of the phased array 20 have the following mathematical relationship:

$$N = (2*n) + 1 \quad (1)$$

$$M = (n+1)*m \quad (2)$$

where n, m are two integers, m is even, and n is typically much smaller than m. The variable n represents the number of pairs of symmetrical rows (i.e., rows 1, 2 and 3) of elements 22 about the center row (i.e., row 0) of the array 20. The variable m represents the number of columns that define the width of the smallest aperture in the azimuthal plane.

Therefore, for the array of FIG. 2, m=8 columns and n=3 pairs of symmetrical rows. The elements 22 of the center row (r=0) are twice the height of the elements of the other rows to increase the height of the array 20 in the elevational direction without increasing the number of elements to the array.

Figure 3:
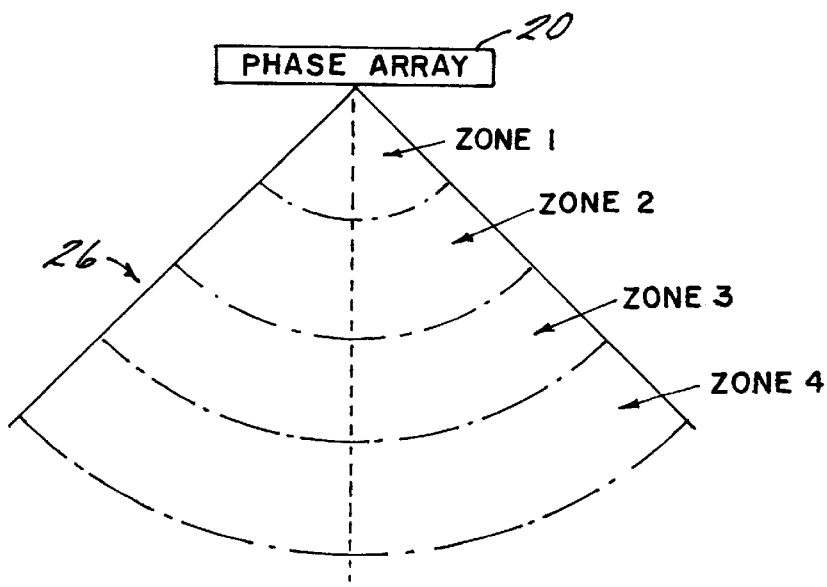
FIG. 3 shows a schematic representation of the imaging zones of an phase array transducer of the present invention.

Referring to FIG. 3, the imaging field 26 of the array 20 is partitioned into four (4) depth zones (Zones 1–4). The number of depth zones is defined by the equation of Z=(n+1), wherein n is the number of pairs of symmetrical rows (r=1–3) about the center row (r=0) of the aperture 24. The aperture shown in FIG. 2, therefore, provides for four zones.

Figure 4A:
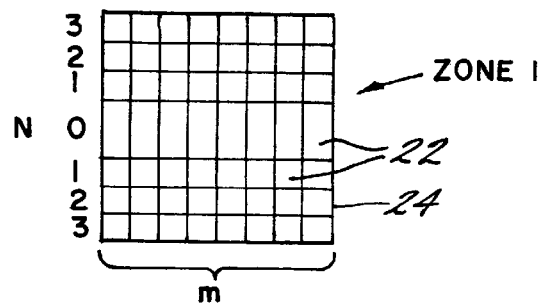
FIGS. 4A–D shows active elements of the array of FIG. 1 for imaging Zones 1–4, respectively, of the FIG. 2.
Figure 4B:
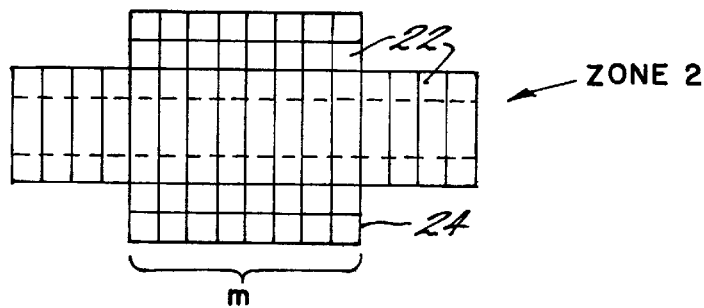
Figure 4C:
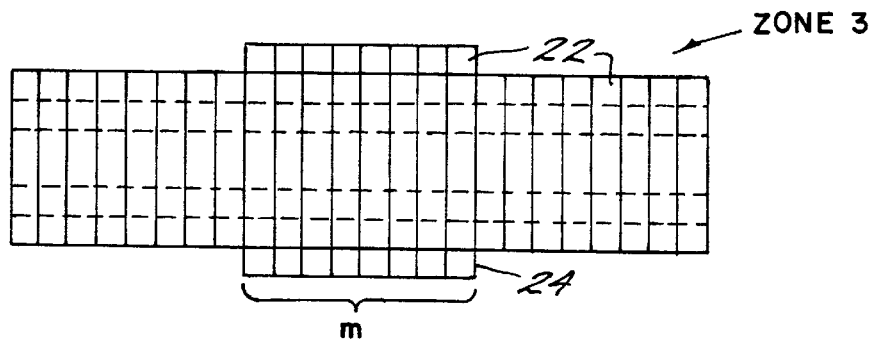
Figure 4D:
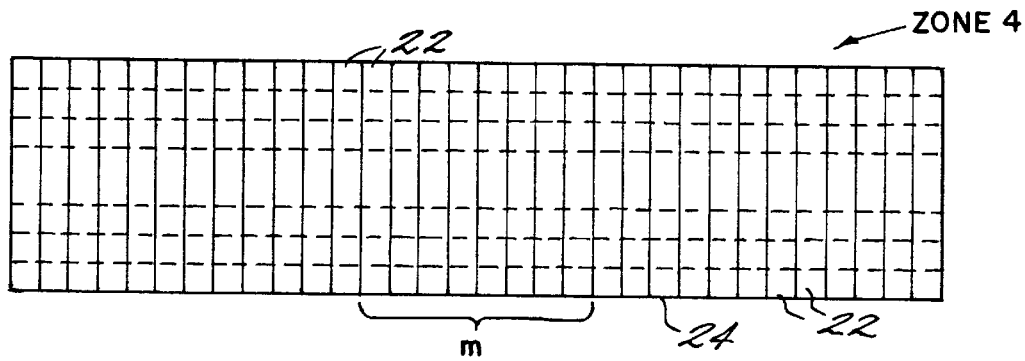

In accordance with the present invention shown in FIGS. 4A–D, a selective number of elements 22 are energized to provide for different aperture shapes and sizes for each zone (Zones 1–4), wherein the first zone (Zone 1) is the nearest imaging field from the array 20, and the fourth zone (Zone 4) is the furthest imaging field from the array. FIG. 4A illustrates an aperture pattern of the activated elements 22 for imaging the first depth zone (Zone 1). FIG. 4B illustrates an aperture pattern of the activated elements 22 for imaging the second depth zone (Zone 2). FIG. 4C illustrates an aperture pattern of the activated elements 22 for imaging the third depth zone (Zone 3). FIG. 4D illustrates an aperture pattern of the activated elements 22 for imaging the fourth depth zone (Zone 4).

The imaging system 10 includes a plurality of beamformer channels 19 (see FIG. 1), which have a pair of beamformers that control the transmitting and receiving of imaging signals to and from the imaging elements 22 of the array 20, as discussed hereinbefore. In the prior art, each imaging element of the aperture 24 requires a beamformer channel 19, thus the array of FIG. 2 would require N*M beamformer channels or 224 beamformer channels.

For the present invention, however, changing the pattern of energized elements 22 for each zone permits the number of beamformer channels 19 required to operate the aperture 24 to be reduced by switching or reallocating the beamformer channels from one element to another element of the array when switching between imaging zones. To further reduce the number of beamformer channels 19, the vertically symmetrical pairs of elements 22 of each column (M) may be interconnected (i.e. rows 1, 2 and 3 of each column). Therefore, only one beamformer channel is required to energize two elements from symmetrical rows. Utilizing this method of interconnecting elements 22 of the aperture 24 and reallocating the beamformer channels between active aperture patterns when switching between depth zones of the imaging field requires a number of beamformer channels 19 equal to the number of columns (M) of the aperture. For example, the apertures 24 of FIGS. 1 and 4A–D requires thirty-two (32) beamformer channels for controlling the energization of the active elements of each active aperture pattern.

The array element's dimensions, aperture shape and size, and the imaging zone depths may be chosen according to various imaging criteria. For example, if it is desired to maintain a certain azimuthal "f-number", the azimuthal dimension of the aperture 24 is increased from zone to zone as illustrated in FIGS. 4A–D.

In the first zone (Zone 1), as shown in FIG. 4A, the dimension of the aperture 24 is such that each of the 32 beamformer channels 19 of the imaging system 10 is allocated to each of the independent elements 22 in the aperture, wherein each vertically symmetrical pair of elements in each row (r=1, 2 and 3) is interconnected, and therefore considered a single element. This configuration allows for the greatest degree of independent delay control for focusing in both azimuth and elevation planes. This configuration also provides the greatest dynamic focusing in the elevational plane.

In the second zone (Zone 1), as illustrated in FIG. 4B, each element pair in the rows immediately above and below the center row (i.e., row 0) for each column (i.e. rows, r=1) is reallocated or connected to the same beamformer channel 19 as the center row element of the respective column (M), as indicated by the broken lines. As a result of reallocating these elements 22, the m (or 8) beamformer channels 19 that controlled the reallocated elements become available for expanding the aperture 24 in the azimuthal plane. The width of the azimuthal aperture is increased by four columns on each side of the prior aperture pattern, where the center row (r=0) and first pair of adjacent rows (r=1) of elements of each added column are interconnected. In other words, 16 channels are allocated to the center row of elements, defined by the center row (row 0) and adjacent rows (rows 1), and 16 channels are allocated to the remaining symmetrical pairs (rows 2 and 3) of elements of center 8 columns.

By interconnecting the elements 22 in the adjacent rows (rows 0 and 1) of the same columns (M), the effective element height of the center row (r=0) is increased which reduces the focusing ability in the elevation plane and thereby, increases the elevation phase error. This phase error can be kept small enough to still improve elevation focusing with the proper choice of element height, mechanical focus depth and zone depth, namely by keeping the elevation "f-number" of the connected elements large.

This element switching and channel reallocation process proceeds from zone to zone, expanding the azimuthal aperture in increments of m (i.e., 8) columns. Referring to FIG. 4C for the third zone, each column (M) of the element pair in the second pair of symmetrical rows (i.e., row 2) of the center m (8) columns are reallocated or connected to the same beamformer channel 19 as the center three elements 22 (r=1, 2, 3) of the respective column, as indicated by the broken lines. As a result of reallocating these elements 22, another m (or 8) beamformer channels 19 that controlled the reallocated elements become available for further expanding the aperture 24 in the azimuthal direction. The width of the azimuthal aperture 24 is increased by four columns on each side of the prior aperture pattern of zone 2, wherein the center row and first and second pair of adjacent rows of elements of each added column are interconnected.

In the fourth zone as shown in FIG. 4D, each column of the element pair in the third row (row 3) of symmetrical elements of the center eight (8) columns are reallocated or connected to the same beamformer channel 19 as the center four elements 22 (r=1, 2, 3, 4) of the respective column, as indicated by the broken lines. As a result of reallocating these elements 22, another m (or 8) beamformer channels 19 become available for expanding the aperture in the azimuthal direction. The width of the azimuthal aperture is increased by four columns on each side of the prior aperture pattern of zone 3, wherein all the elements of each added column are interconnected with the center row.

The interconnection of all the rows (N) of each column (M) eliminates elevational focusing of the aperture 24 and therefore, the elevation focusing in each column is provided only by the mechanical elevation focusing, such as a lens or element shaping, the total element height controlled by how many elements in the column are connected together, and in one implementation of the invention by elevational apodization. The mechanical focus depth is chosen to be in the far field (i.e., Zone 4), as opposed to the conventional approach of focusing at the depth of highest interest, typically in the middle of the imaging field. Thus, good elevation focusing is achieved in the far field without the need for electronic beamforming delays. In addition, since the "f-number" is large in the far field, the depth of focus will be large.

The depth-dependent aperture reconfiguration method is best used in the multi-zone imaging mode used by most ultrasound imaging systems to provide multiple transmit focal depths. In this mode each scan line is assembled from multiple segments, one for each depth zone, where each segment is acquired from a separate transmit focused at a point in the respective zone. However, the method can also be used with scan lines acquired from only one transmitted beam per line, with the aperture 24 configured in the optimal way for the desired transmit focal depth, with or without dynamic receive aperture configuration.

Figure 5:
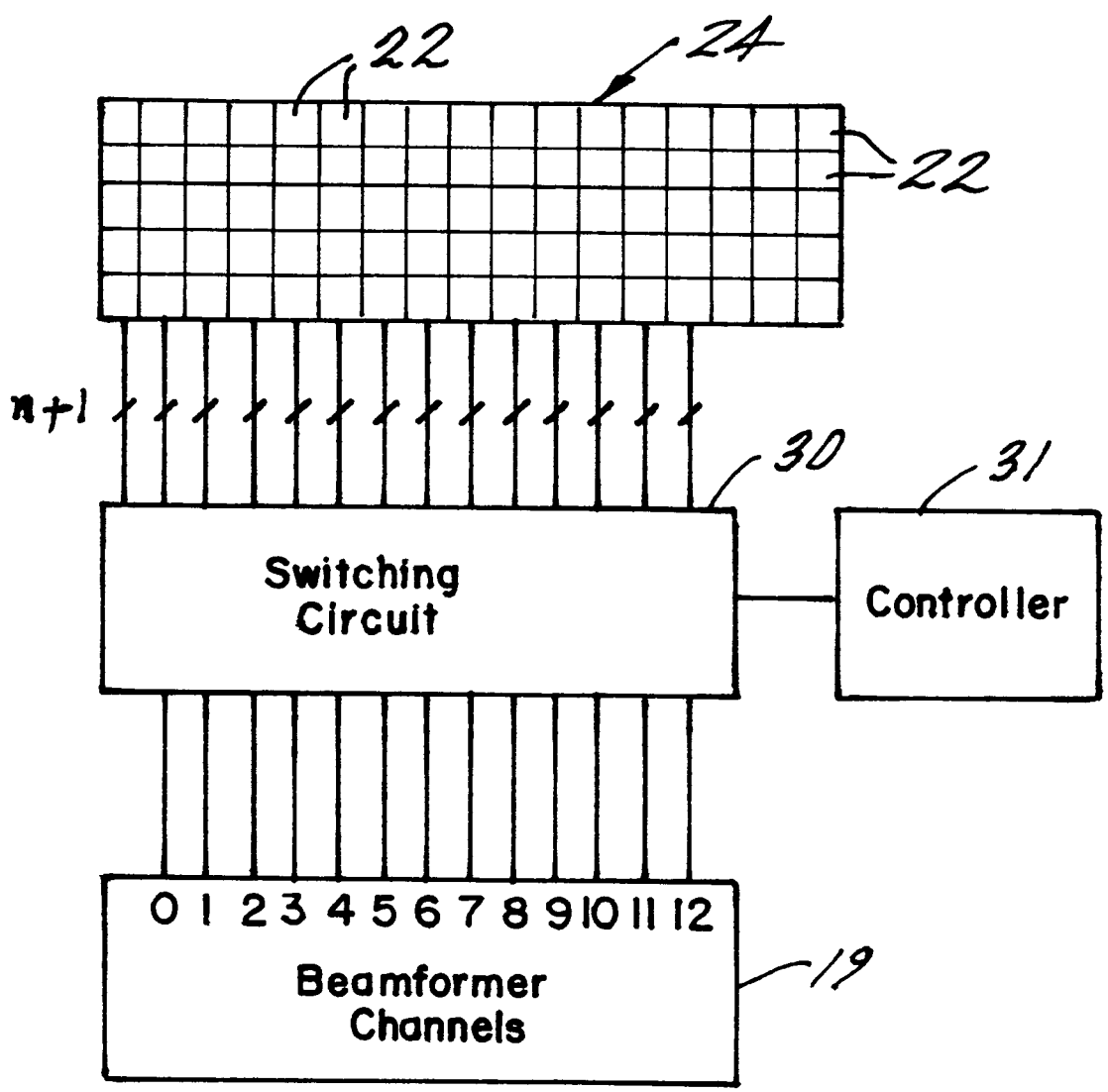
FIG. 5 shows a schematic view of a transducer and a switching circuit employed by the present invention.

As shown in FIG. 5, a switching circuit is provided between the aperture elements 22 and the beamformer channels 19 which includes programmable switches for connecting the elements 22 to the channels in accordance with a number of switching methods as will be described hereinafter. The switches 34 are controlled by a controller 31 that actuates the switching in response to a computer program.

Figures 6A, 6B, 6C:
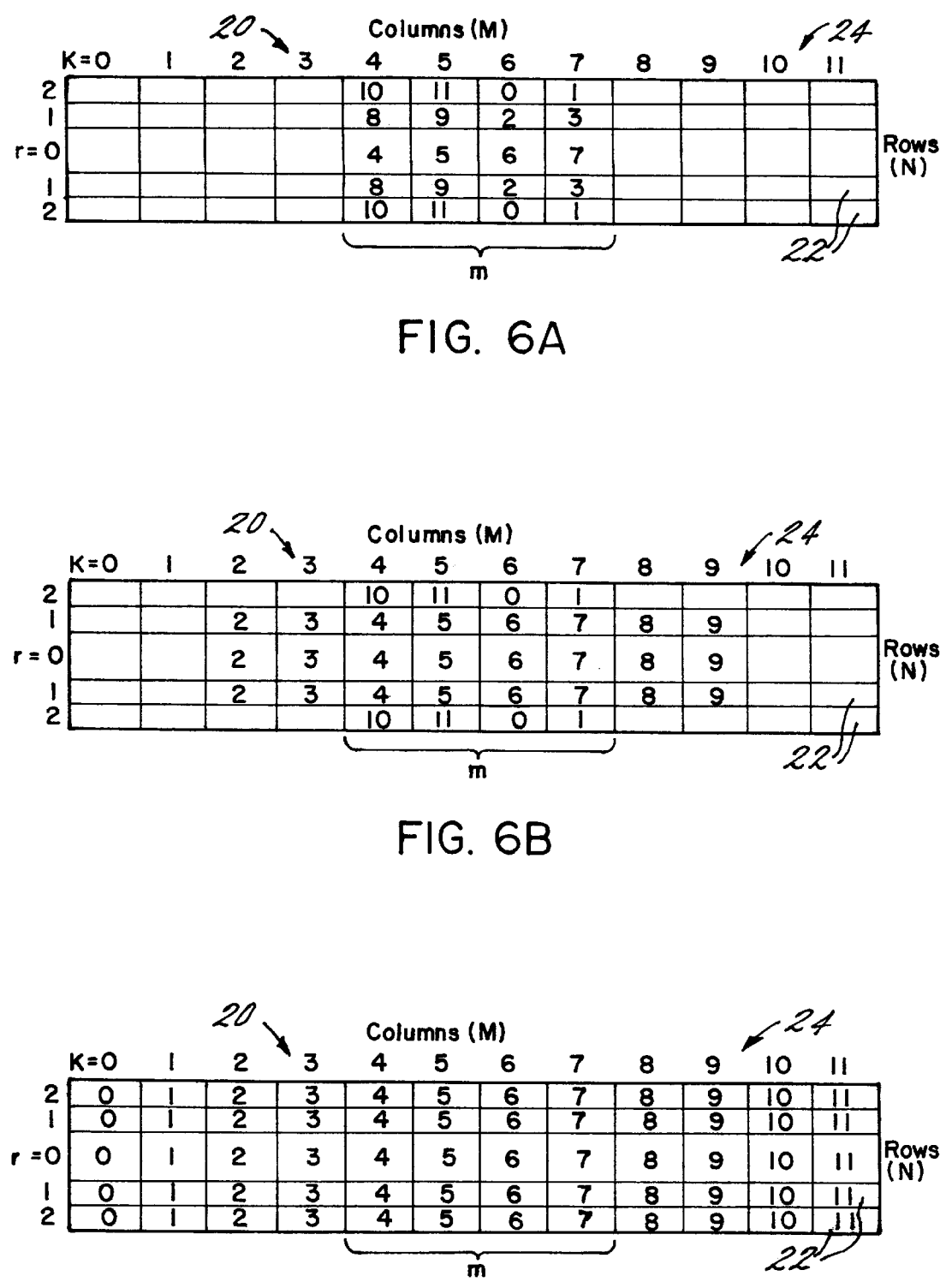

One such element switching method for an aperture 24 of a phase array 20 is illustrated in FIGS. 6A–C. The aperture has twelve (M=12) columns and five (N=5) rows, wherein n=2 and m=4. Similar to the array shown in FIGS. 4A–D, the symmetrical pair of rows (r=1, 2) of elements 22 about the center row (r=0) of elements of each column are interconnected together. The imaging system 10, therefore, requires M number (12) of beamformer channels 19, numbered 0–11, to control the elements of the aperture 24. As discussed above, the aperture having two (n=2) pairs of symmetrical rows of elements provides for an array 24 for imaging three depths of field or zones (i.e. Z=n+1). FIG. 6A represents the active aperture pattern for Zone 1, the nearest imaging field. FIG. 6B represents the active aperture pattern for Zone 2, the intermediate imaging field. FIG. 6C represents the active aperture pattern for Zone 3, the furthest imaging field.

In the aperture 24 shown in FIGS. 6A–C, the allocation of each beamformer channel 19 is shown for each active element 22 of the aperture within each of the elements. For example, beamformer channel 1 is connected to the elements in the outer symmetrical pair (rows 2) in column seven (7), and channel 9 is connected to the elements in the symmetrical pair (rows 1) in column five (5). It should be noted that the columns are numbered from zero to (M-1) (i.e., k=0–11), wherein the column number is represented by the variable k.

As described hereinbefore, as the aperture pattern changes from Zone 1 to Zone 3, the beamformer channels 19 that are connected to the symmetrical rows (r=1, 2) of elements about the center row (r=0) switch to the outer columns to increase the azimuthal width of the aperture 24. As illustrated in FIGS. 6A–C, the elements 22 in the center row (r=0) of the m central columns (k=4–7) are permanently connected to m beamformer channels (channels 4–7, respectively). The element pairs in the $r'^{th}$ pair of off-center rows (r=1, 2) of the m central columns (k=4–7) have 2 switches each, first of which connects the element pair to the beamformer channel 19 of the center row (r=0) of their column, and the second switch to the beamformer channel they share with one of the columns which is added to the aperture 24 for azimuthal expansion in the (r+1)'s zone. For example, in FIGS. 6A–C, the pair of elements of row 1 of column 6 are connected to channel 2 via a first switch (for Zone 1) (FIG. 6A) and to channel 6 via a second switch (for Zones 2 and 3) (FIGS. 6B and 6C, respectively). In addition, the pair of elements 22 of row 2 of column 4 are connected to channel 10 via a first switch (for Zones 1 and 2) (FIGS. 6A and 6B, respectively) and to channel 4 via a second switch (for Zone 3) (FIG. 6C).

It should be noted that the method or configuration of allocating the beamformer channels 19 to the imaging elements 22 as shown in FIGS. 6A–C is but one method of allocating the beamformer channels. Four configurations (including the configuration of FIGS. 6A–C provide the maximum flexibility in controlling the aperture shape, and allowing the aperture 24 to azimuthally expand in any desired column increment, not necessarily m.

One such configuration of switching of the beamformer channels to the adjacent columns M to increase the azimuthal aperture is shown in FIGS. 6A–C. The allocation of the beamformer channels 19 to the element pairs of the m central columns (k=4–7) and the adjacent columns are defined by the following equations:

$$\text{Added Column} = k + [(r+1)*m/2] \quad (3)$$

$$\text{Added Column} = k - [(r+1)*m/2] \quad (4)$$

where k represents the column number, r represents the row pair and m represents the number of columns that define the width of the smallest aperture pattern in the azimuthal plane.

Figure 7A:
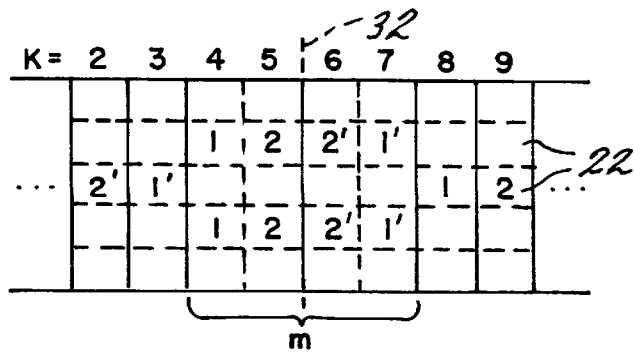
FIG. 7A shows a schematic view of the first allocation method for switching the beamformer channels between the imaging elements.

FIG. 7A schematically illustrates the basic allocation of the off center rows r as the aperture pattern changes from zone to zone in accordance with equations (3) and (4). The configuration of the aperture switching circuit switches the beamformer channels 19 from the off-center element pairs disposed to the left of the center 32 of the aperture 24 to the elements 22 of the columns M expanded to the right half, and switches the beamformer channels from the off-center element pairs disposed to the right of the center 32 of the aperture 24 to the elements of the columns M expanded to the left half. In addition the order of adding the adjacent columns is relative to the off-center element pair's relationship to the center 32 of the aperture 24. For this configuration, the element pair (i.e., 1, 1') furthest from the center 32 of the aperture 24 is added first to the opposite end of the active aperture when switching from one zone to the next. The element pair (i.e., 2, 2') next furthest from the center 32 of the aperture 24 is added second to the opposite end of the active aperture, and so on. For example, beamformer channel 1' which is initially connected to the element pair disposed to the right of the center 32 of the aperture in column 7 is switched to the first column (k=3) to the left of the active aperture when the aperture is expanded from zone to zone. Furthermore, beamformer channel 2', which is initially connected to an element pair in column 6, is switched to the second column (k=2) when the azimuthal aperture is expanded.

Therefore, equation (3) is used to allocate the beamformer channels 19 to the off-center pairs (r=1, 2) disposed to the left of the center 32 of the aperture 24. For example referring to FIGS. 6A–C, the off-center pair in row 2 (r=2) of column 4 (k=4) is allocated to beamformer channel 10, which is also allocated to the elements of column 10, where the width of the central aperture is equal to 4 (m=4).

Similarly, equation (4) is used to allocate the beamformer channels 19 to the off-center pairs (r=1, 2) disposed to the right of the center 32 of the aperture 24. For example, the off-center pair in row 1 (r=1) of column 7 (k=7) is allocated to beamformer channel 3, which is also allocated to the elements of column 3, where the width of the central aperture is equal to 4 (m=4).

Figure 7B:
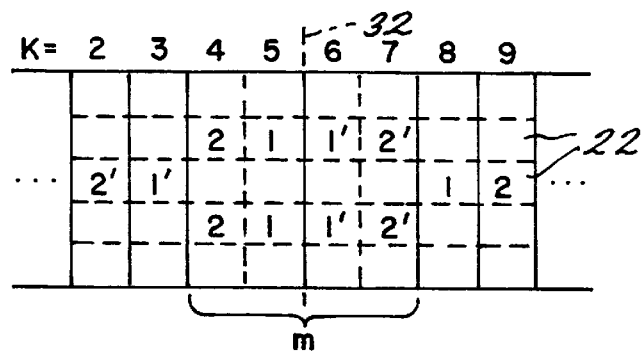
FIG. 7B shows a schematic view of a second allocation method for switching the beamformer channels between the imaging elements.

A second configuration of switching of the elements pairs (r=1, 2) to the adjacent columns (M) to increase the azimuthal aperture is shown schematically in FIG. 7B. The allocation of the beamformer channels 19 to the element pairs of the m central columns (k=4–7) and the adjacent columns are defined by the following equations:

$$\text{Added Column} = (n*m) - k + [(r+2)*m/2] - 1 \quad (5)$$

$$\text{Added Column} = [(n+2)*m)] - k - [(r+2)*m/2] - 1 \quad (6)$$

where k represents the column number, r represents the row pair and m represents the number of columns that define the width of the smallest aperture pattern in the azimuthal plane.

FIG. 7B schematically illustrates the basic allocation of the off center rows r as the aperture pattern changes from zone to zone in accordance with equations (5) and (6). The configuration of the aperture switching circuit 30 (See FIG. 5) switches the beamformer channels 19 from the off-center element pairs disposed to the left of the center 32 of the aperture 24 to the elements of the columns M expanded to the right half, and switches the beamformer channels from the off-center element pairs disposed to the right of the center 32 of the aperture 24 to the elements of the columns expanded to the left half. In addition the order of adding the adjacent columns is relative to the off-center element pair's relationship to the center 32 of the aperture 24. For this configuration, the element pair (i.e., 1, 1') closest to the center 32 of the aperture is added first to the opposite end of the active aperture when switching from one zone to the next. The element pair next closest to the center 32 of the aperture 24 is added second to the opposite end of the active aperture, and so on. For example, beamformer channel 1', which is initially connected to the element pair disposed to the right of the center 32 of the aperture in column 6, is switched to the first column (k=3) to the left of the active aperture when the aperture is expanded from zone to zone. Furthermore, beamformer channel 2', which is initially connected to an element pair in column 7, is switched to the second column (k=2) when the azimuthal aperture is expanded.

Therefore, equation (5) is used to allocate the beamformer channels 19 to the off-center pairs (r=1, 2) disposed to the left of the center 32 of the aperture 24. For example referring to FIG. 8, the off-center pair in row 2 (r=2) of column 4 (k=4) is allocated to beamformer channel 11, which is also allocated to the elements of column 11, where the width of the central aperture is equal to 4 (m=4).

Similarly, equation (6) is used to allocate the beamformer channels 19 to the off-center pairs (r=1, 2) disposed to the right of the center 32 of the aperture 24. For example, the off-center pair in row 1 (r=1) of column 7 (k=7) is allocated to beamformer channel 2, which is also allocated to the elements of column 2, where the width of the central aperture is equal to 4 (m=4).

Figure 7C:
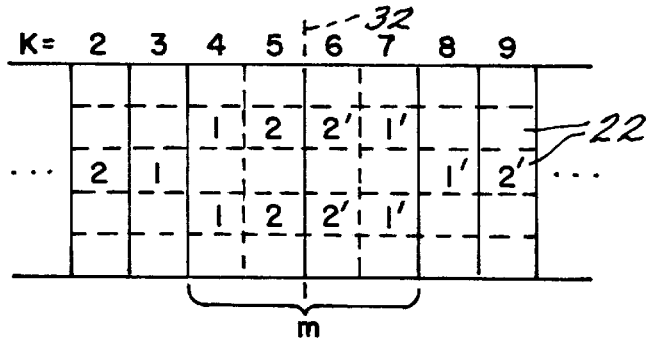
FIG. 7C shows a schematic view of a third allocation method for switching the beamformer channels between the imaging elements.

A third configuration of switching of the elements pairs (r=1, 2) to the adjacent columns (M) to increase the azimuthal aperture is shown schematically in FIG. 7C. The allocation of the beamformer channels 19 to the element pairs of the m central columns (k=4–7) and the adjacent columns are defined by the following equations:

$$\text{Added Column} = (n*m) - k - [(r-1)*m/2] - 1 \quad (7)$$

$$\text{Added Column} = [(n+2)*m)] - k + [(r-1)*m/2] - 1 \quad (8)$$

where k represents the column number, r represents the row pair and m represents the number of columns that define the width of the smallest aperture pattern in the azimuthal plane.

FIG. 7C schematically illustrates the basic allocation of the off center rows r as the aperture pattern changes from zone to zone in accordance with equations (7) and (8). The configuration of the aperture switching circuit 30 (see FIG. 5) switches the beamformer channels 19 from the off-center element pairs disposed to the left of the center 32 of the aperture 24 to the elements of the columns M expanded to the left half, and switches the beamformer channels from the off-center element pairs disposed to the right of the center 32 of the aperture 24 to the elements of the columns expanded to the right half. In addition the order of adding the adjacent columns is relative to the off-center element pair's relationship to the center 32 of the aperture 24. For this configuration, the element pair (i.e., 1, 1') furthest from the center 32 of the aperture 24 is added first to the same end of the active aperture when switching from one zone to the next. The element pair next furthest from the center 32 of the aperture is added second to the opposite end of the active aperture, and so on. For example, beamformer channel 1, which is initially connected to the element disposed to the right of the center 32 of the aperture in column 7, is switched to the first column (k=8) to the right of the active aperture 24 when the aperture is expanded from zone to zone. Furthermore, the beamformer channel 2', which is initially connected to an element pair in column 6, is switched to the second column (k=9) when the azimuthal aperture is expanded.

Therefore, equation (7) is used to allocate the beamformer channels 19 to the off-center pairs (r=1, 2) disposed to the left of the center 32 of the aperture 24. For example referring to FIG. 9, the off-center pair in row 2 (r=2) of column 4 (k=4) is allocated to beamformer channel 1, which is also allocated to the elements of column 1, where the width of the central aperture is equal to 4 (m=4).

Similarly, equation (8) is used to allocate the beamformer channels 19 to the off-center pairs (r=1, 2) disposed to the right of the center 32 of the aperture 24. For example, the off-center pair in row 1 (r=1) of column 7 (k=7) is allocated to beamformer channel 8 which is also allocated to the elements of column 8, where the width of the central aperture is equal to 4 (m=4).

Figure 7D:
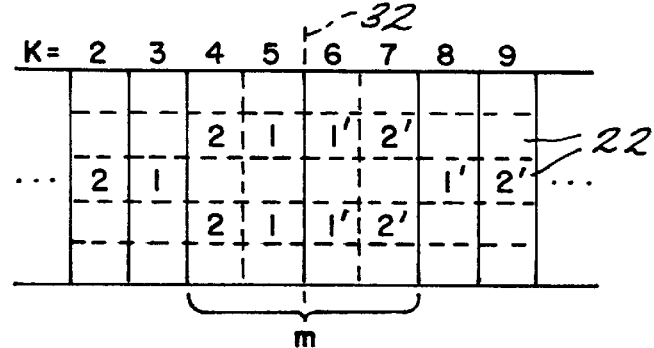
FIG. 7D shows a schematic view of a fourth allocation method for switching the beamformer channels between the imaging elements.

A fourth configuration of switching of the elements pairs (r=1, 2) to the adjacent columns M to increase the azimuthal aperture is shown schematically in FIG. 7D. The allocation of the beamformer channels 19 to the element pairs of the m central columns (k=4–7) and the adjacent columns are defined by the following equations:

$$\text{Added Column}=k-[r^*m/2] \quad (9)$$

$$\text{Added Column}=k+[r+m/2] \quad (10)$$

where k represents the column number, r represents the row pair and m represents the number of columns that define the width of the smallest aperture pattern in the azimuthal plane.

FIG. 7D schematically illustrates the basic allocation of the off center rows r as the aperture pattern changes from zone to zone in accordance with equations (9) and (10). The configuration of the aperture switching circuit 30 (see FIG. 5) switches the beamformer channels 19 from the off-center element pairs disposed to the left of the center 32 of the aperture 24 to the elements of the columns M expanded to the left half, and switches the beamformer channels from the off-center element pairs disposed to the right of the center 32 of the aperture to the elements of the columns expanded to the right half. In addition the order of adding the adjacent columns is relative to the off-center element pair's relationship to the center 32 of the aperture. For this configuration, the element pair (i.e. 1, 1') closest to the center 32 of the aperture 24 is added first to the same end of the active aperture when switching from one zone to the next. The element pair the next closest to the center 32 of the aperture is added second to the opposite end of the active aperture, and so on. For example, beamformer channel 1' which is initially connected to the element disposed to the right of the center 32 of the aperture in column 6 is switched to the first column (k=8) to the right of the active aperture when the aperture is expanded from zone to zone. Furthermore, the right beamformer channel 2', which is initially connected to an element pair in column 7, is switched to the second column (k=9) when the azimuthal aperture is expanded.

Therefore, equation (9) is used to allocate the beamformer channels 19 to the off-center pairs (r=1, 2) disposed to the left of the center 32 of the aperture 24. For example referring to FIG. 10, the off-center pair in row 2 (r=2) of column 4 (k=4) is allocated to beamformer channel 0, which is also allocated to the elements of column 0, where the width of the central aperture is equal to 4 (m=4).

Similarly, equation (10) is used to allocate the beamformer channels 19 to the off-center pairs (r=1, 2) disposed to the right of the center 32 of the aperture 24. For example, the off-center pair in row 1 (r=1) of column 7 (k=7) is allocated to beamformer channel 9, which is also allocated to the elements of column 9, where the width of the central aperture is equal to 4 (m=4).

Figure 11:
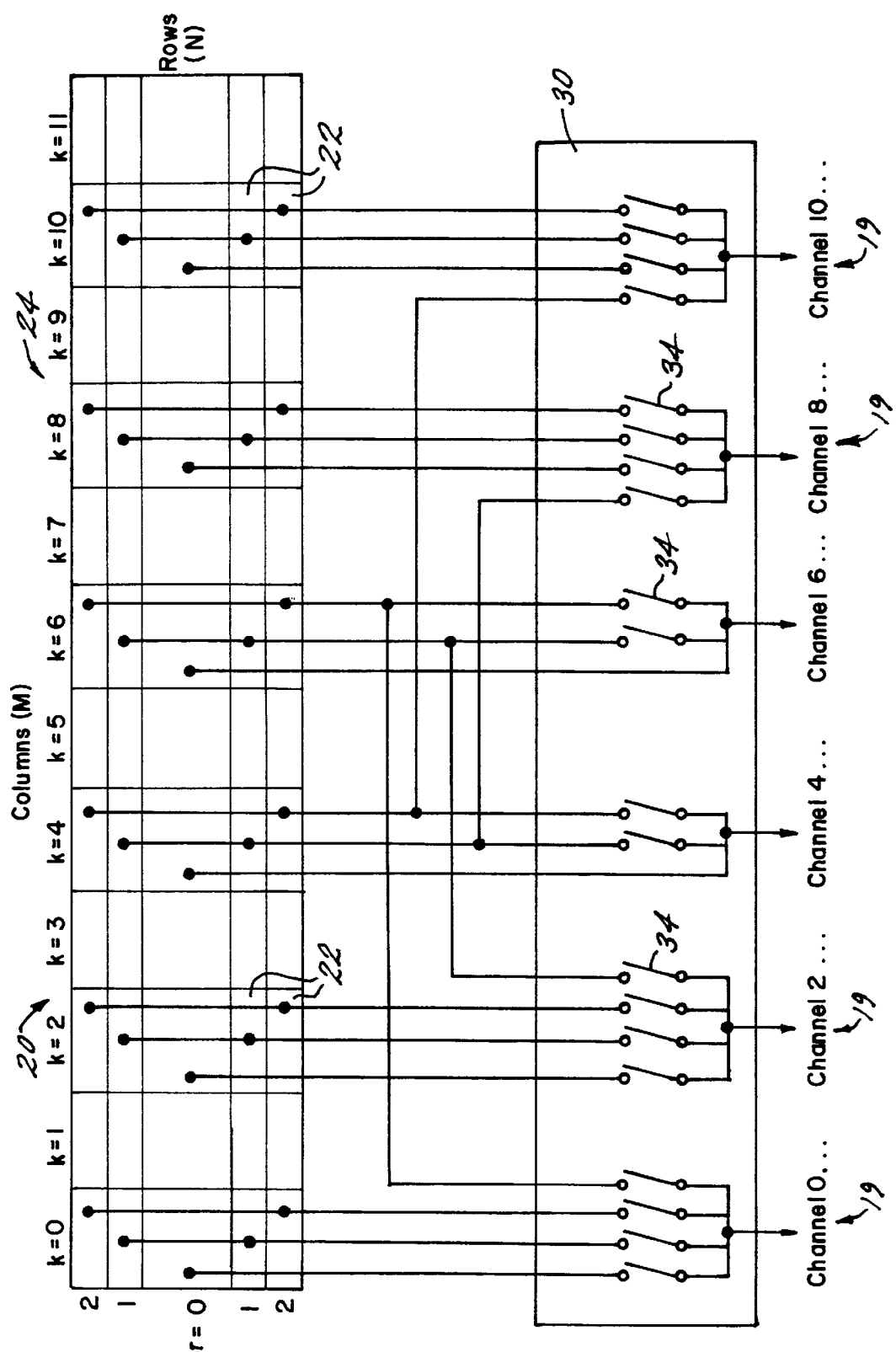
FIG. 11 shows a schematic representation of an aperture of transducer of FIG. 1 and switching circuit in accordance with the first allocation method.

Referring to FIG. 11, implementation of the methods described above requires the use of a switching circuit 30 for reprogramming the connections between the aperture elements 22 and the beamformer channels 19. FIG. 11 illustrates the interconnections between the switching circuit and even numbered columns with the understanding that the odd numbered columns are similarly connected to the switching circuit.

The switching circuit 30 shown in FIG. 11 is illustrative of the first configuration of FIGS. 6A–C. In the case of phased array probes, the structure of the switching circuit 30, as described above, is such that the elements 22 in the central row (r=0) of the m central columns (k=4–7) are permanently connected to corresponding m beamformer channels 19. For example, the center elements 22 of columns 4–7 are directly connected to the beamformer channels 4–7, respectively. The element pairs in the $r^{\prime th}$ off-center rows (r=1, 2) of the m central columns (k=columns 4–7) have 2 switches 34 each, first of which connects them to the beamformer channel of the center row of their column, and the second to the beamformer channel 19 they share with one of the columns M which is added to the aperture for azimuthal expansion in the (r+1) zone. For example, the second off-center row (r=2) of the fourth column (k=4) is connected via a pair of switches 34 to channel 4 and channel 10.

Further the elements 22 in the central row (r=0) of all columns, other than the m central columns 4–7 have one switch 34 each, which connects them to the corresponding beamformer channels when the aperture 24 is expanded to include their columns. The element pairs in the off-center (r=1, 2) rows of all columns (other than the m central columns (k=4–7)) have one switch 34 each, which connects them to the beamformer channels 19 of the center row (r=0) of their column when their column and row are included in the active aperture 24.

Figure 12:
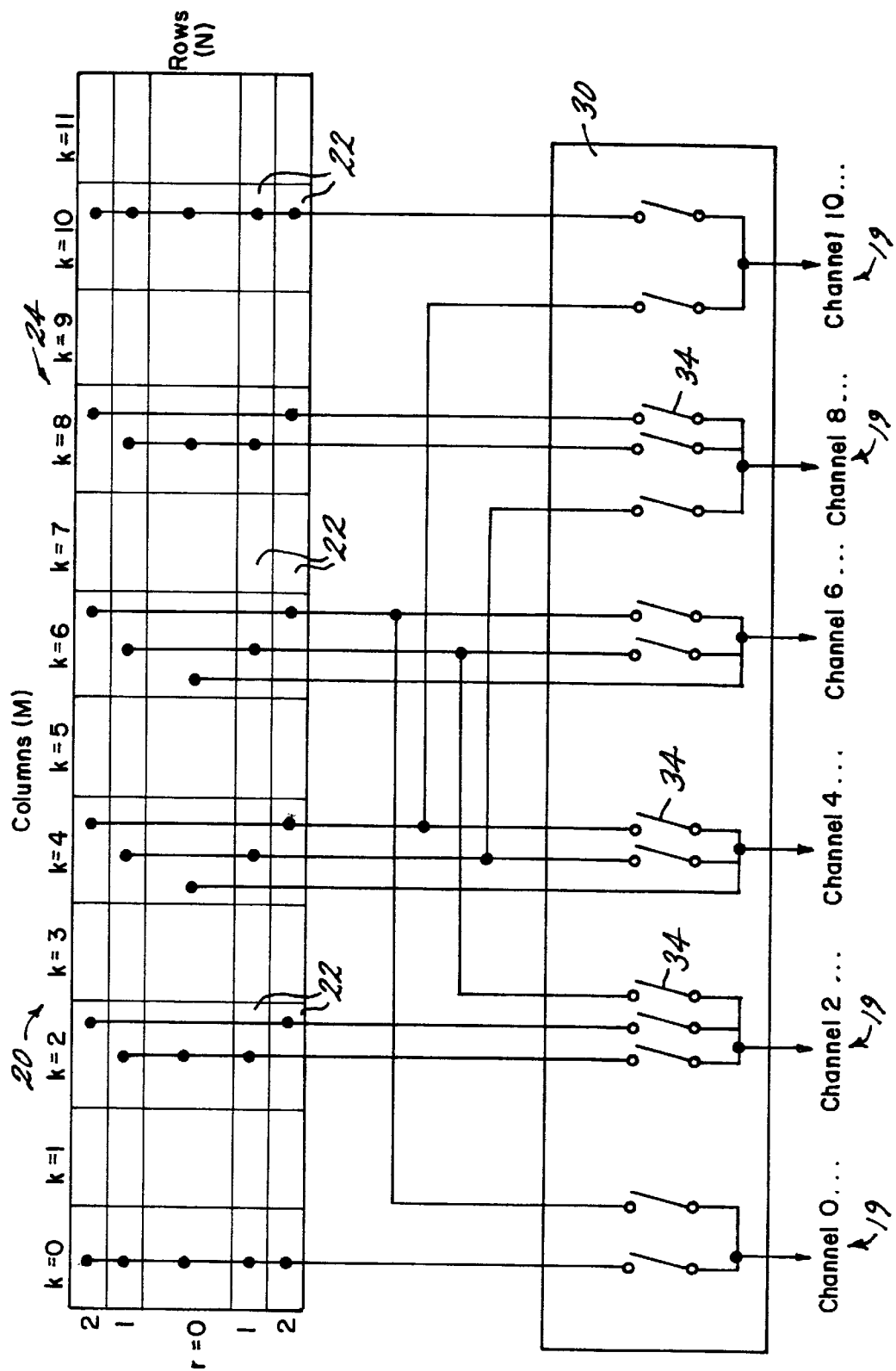
FIG. 12 shows a schematic representation of an alternative embodiment of the aperture of transducer of FIG. 1 and switching circuit in accordance with the first allocation method.

It can be seen that for the aperture configuration for Zones 1–3 of FIGS. 6A–C for the phased array 20 shown in FIG. 11 requires n*m*(n+3) switches, or 40 switches 34, where n=2 and m=4. The number of switches, however, can be reduced by hardwiring a selected number of the off-center element pairs (r=1, 2) as shown in FIG. 12. For each added column (k=2, 3, 8, 9) for Zone 2, the center row (r=0) of elements 22 and the first row (r=1) of off-center element pairs are hardwired together. For each added column (k=0, 1, 10, 11) for Zone 3, the center row (r=0) of elements and all off-center element pairs (r=1, 2) are hardwired together. Hardwiring the off-center element pairs reduces the number of switches 34 from forty (40) to twenty-eight (28) without changing the configuration of the aperture 24.

Figure 13:
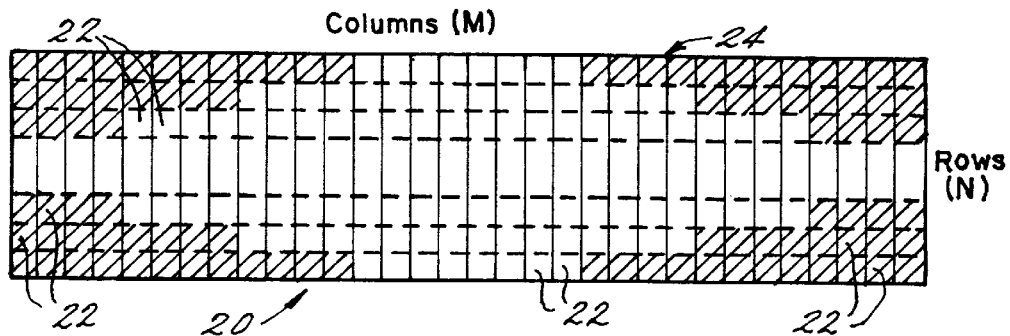
FIG. 13 shows a schematic representation of an alternative embodiment of the aperture of FIG. 1.

Another method of reducing the number of switches 34 required to reallocate the elements 22 of the aperture 24 is to eliminate or reduce the number of elements for the active aperture. For example, it is known that an approximately elliptical aperture 24 as shown in FIG. 13 produces focusing characteristics better in some respects compared to a rectangular aperture. Therefore, some of the elements in the corners of the array 24 (shaded areas) are not used, to thereby reduce the number of switches 34 from n*m*(n+3)=144 switches to 96 switches, where n=3 and m=8.

It can, therefore, be appreciated that a combination of the technique of hardwiring selective elements 22 of a column M, and the technique of eliminating elements from the active aperture 24 will further reduce the number of switches 34 necessary to reallocate the elements of the array 20. For example, selectively hardwiring elements 22 of the aperture 24 configuration of FIG. 13 further reduces the switch count from 96 to 80 switches 34. This is especially true for large arrays such as an array 20 having 128 columns and 7 rows which reduces the switch count to 320 switches, 34 compared to 576 switches for a fully populated switch configuration.

Figure 14:
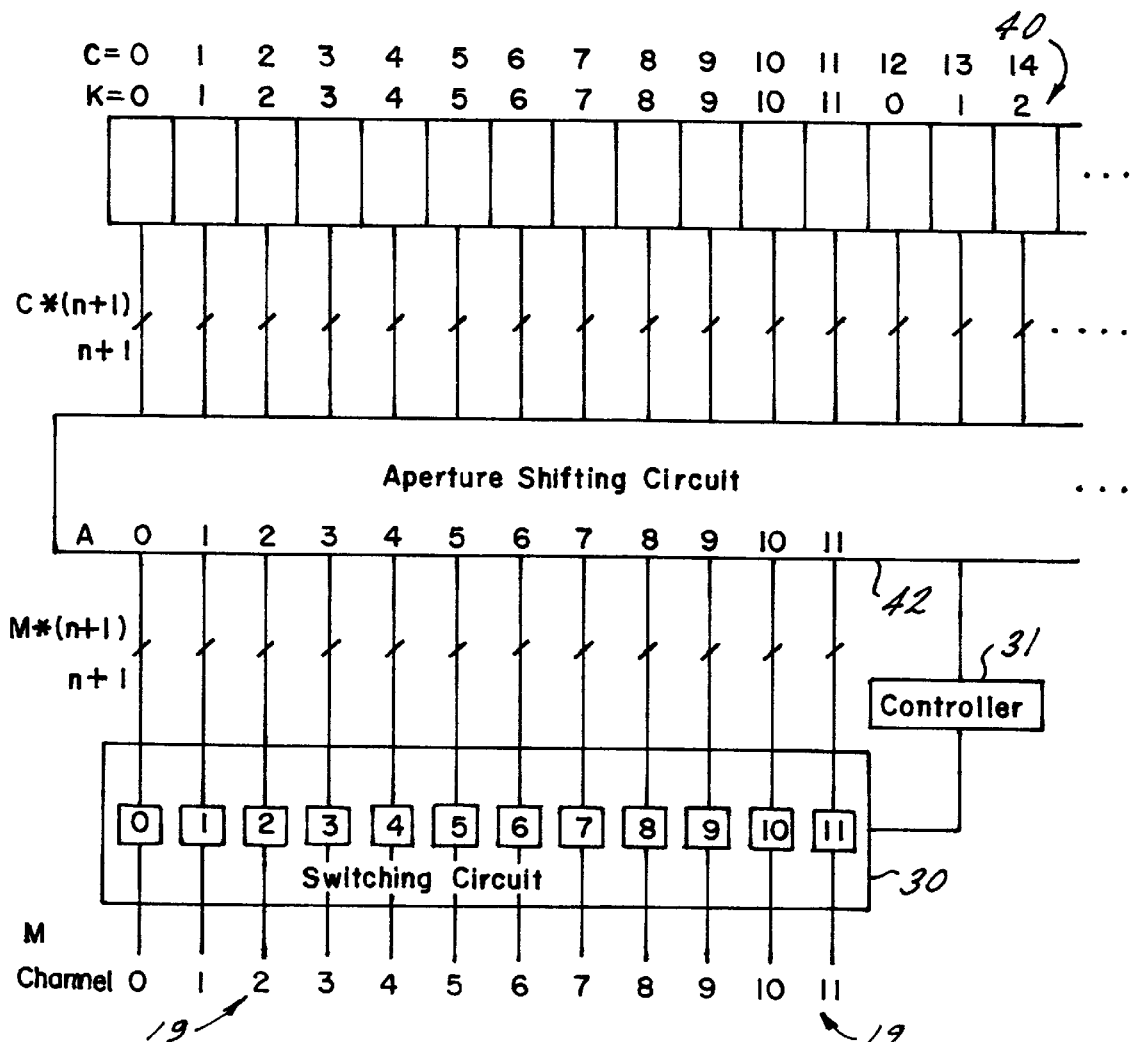
FIG. 14 shows a schematic representation of an ultrasound imaging system having a linear/convex array wherein an aperture shifting circuit precedes a switching circuit.

FIG. 14 illustrates a method of allocating the imaging elements 22 of a linear/convex array 40 to a plurality of beamformer channels 19 to provide dynamic elevational focusing of the imaging beam using a reduced number of beamformer channels 19. In addition to a switching circuit 30, similar to that described hereinbefore, the element allocation system for linear/convex arrays 40 further requires a shifting circuit 42 for shifting or positioning the aperture 24 along the azimuthal direction of the array 40.

Figure 15A:
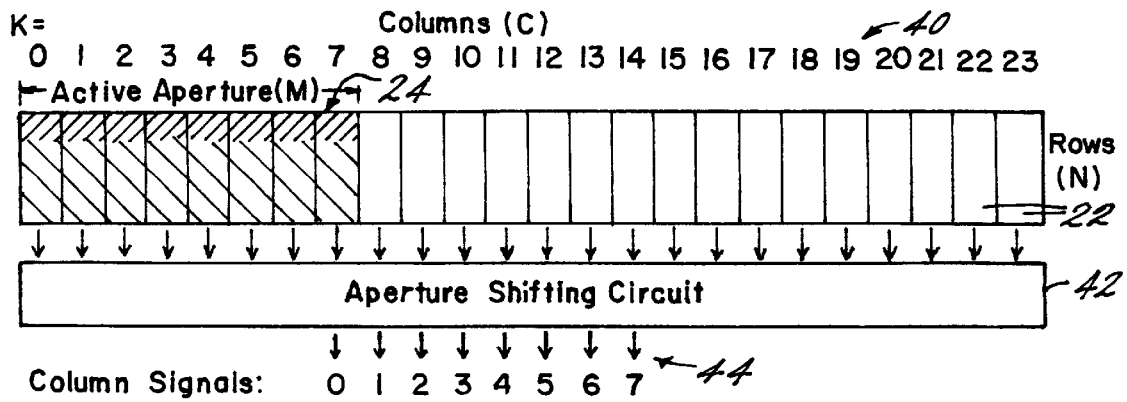
FIGS. 15A–C show a schematic representation of an aperture and aperture shifting circuit illustrating the shifting of the aperture along the azimuth direction of a linear/convex array.
Figure 15B:
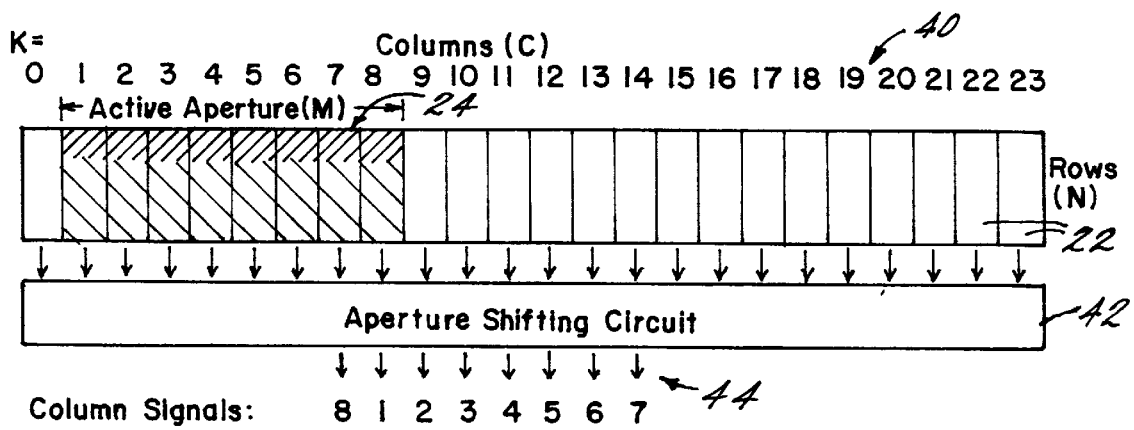
Figure 15C:
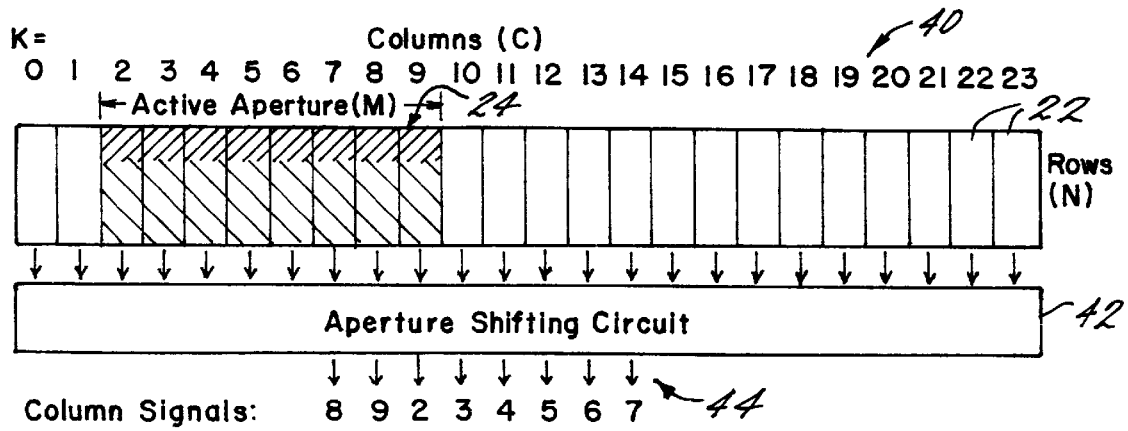

FIGS. 15A–C illustrate the shifting operation of the columns M of an aperture shifting circuit 42. As described hereinbefore, the active aperture 24 for each scan line in linear/convex arrays 40 is a different subset of the array's elements 22. The linear array 40, as shown, comprises twenty-four (24) element columns (C), identified as k=0–23, with an active aperture 24 composed of eight (8) element columns (M). The aperture shifting circuit 42 includes a plurality of switches (not shown) that shift the active aperture by one column along the array 40. Shifting the aperture 24 in the azimuthal direction by one element column (C), for example from left to right, is achieved by disconnecting the leftmost element column of the current aperture 24 and connecting it to the next column to the right of the active aperture. As a result, the aperture columns appear at the output 44 of the aperture shifting circuit in a different, rotated order. For example, in FIG. 15A the aperture columns (M) appear at the output 44 of the aperture shifting circuit 42 in the order k=0, 1 ... (M−1). When the aperture 24 is shifted to the right by one position, as shown in FIG. 15B, the order of the aperture columns (M) that appear at the output 44 of the aperture shifting circuit 40 is (M−1), 0, 1 ... (M−2). When the aperture 24 is shifted to the right by another position, as shown in FIG. 15C, the order of the aperture columns (M) that appear at the output 44 of the aperture shifting circuit 40 is (M−2), (M−1), 0, 1 ... (M−3).

As the aperture 24 shifts in the azimuthal direction, most element columns (C) will occupy each azimuthal position relative to the center 32 of the aperture. The same element 22, therefore, may be located in the right or left half of the aperture 24, depending on the position of the aperture. Each of the pair of off-center row elements are connected to a beamformer channel 19 that is dependent on the position of the element relative to the center 32 of the aperture 24, (which will be described in greater detail hereinafter).

The element allocation system may include a plurality of different configurations for shifting the azimuth aperture and switching the allocation of the beamformer channels 19 to the elements 22 of the array 40. The imaging systems differ by the position of the switching circuit 30 for elevation focusing relative to the aperture shifting circuit 42, commonly used in ultrasound scanners, whose operation was briefly described above.

Referring to FIG. 14, a first embodiment of an array element allocation system for a linear/convex array 40 may be configured such that the aperture shifting circuit 42 precedes the switching circuit 30. The aperture shifting circuit 42 receives all the signals (C*[n+1] signals), provided from the linear array 40 with the understanding that the off-center pairs symmetrical about each center element 22 of each column (C) are interconnected to transmit and receive a single signal. Therefore, the total number of signals provided by each column (C) equals n+1, wherein n=the number of pairs of off-center rows of elements 22. The aperture shifting circuit 42 provides M*(n+1) signals to the switching circuit 30, wherein M=the number of columns of the aperture 24. The switching circuit then connects selected channel signals of the elements to the beamformer channels 19 to activate the appropriate aperture pattern for each zone of the imaging field 26 (see FIG. 3). The switching circuit 30 has M outputs connected to the M pairs (transmit and receive) of beamformer channels 19. The switches of the aperture shifting circuit 42 and the switching circuit 30 are actuated by a control signal provided by the controller 31 in response to a computer program.

In this configuration the column index A refers to the columns of signals at the output of the aperture shifting circuits 42, which do not generally correspond to the aperture columns (M) in their left-to-right order, but rather to their rotated order function of the aperture position, as described hereinbefore.

Figure 16:
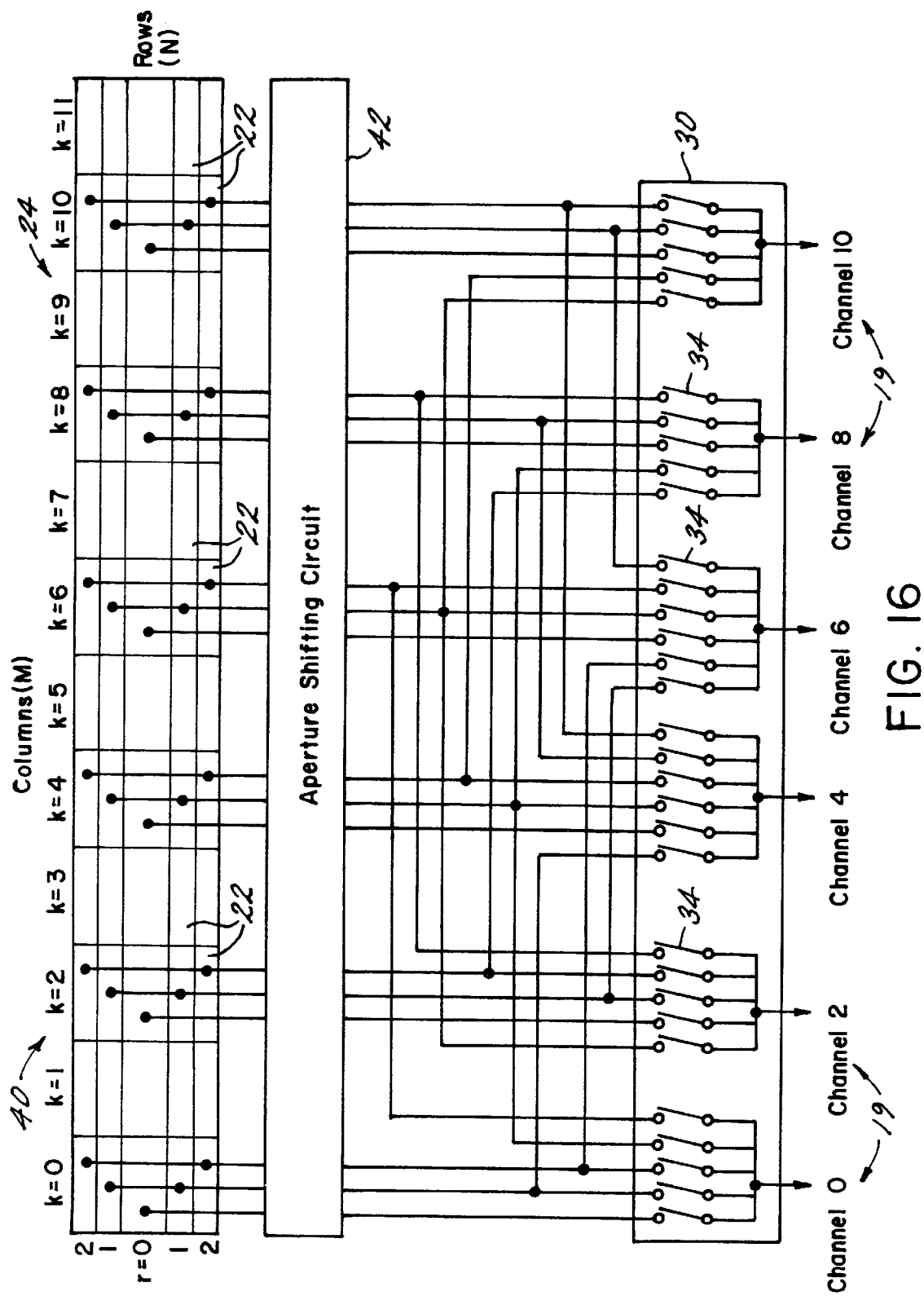
FIG. 16 shows a schematic representation of an aperture of the transducer of FIG. 15, aperture shifting circuit and switching circuit in accordance with a first allocation method.

Referring to FIG. 16, the switching circuit 30 provides programmable switches 34 for each element signal provided as an input to the switching circuit from the aperture shifting circuit 42. Only the even numbered channels 19 and corresponding switches 34 are shown, with the understanding that the odd number channels and switches are similarly interconnected. Further, only twelve (12) columns of the total number of columns (C) of the array are shown. The following connectivity equations define the interconnection of each element signal to a corresponding beamformer channel 19:

$$E_{rk} = k \tag{7}$$

$$F_{rk} = (k + [(r+1)*m/2]) \bmod M \tag{8}$$

$$G_{rk} = (M + k - [(r+1)*m/2]) \bmod M \tag{9}$$

where the operator mod (modulo, remainder of integer division) causes the column indexes to 'wrap around' when exceeding the M−1 value in the same manner in which the aperture columns (M) are rotated at the output of the aperture shifting circuit 42.

$E_{rk}$ represents the interconnection between a central element 22 of the $k^{th}$ column of the aperture 24 and a beamformer channel 19. $F_{rk}$ represents the interconnection between an element pair of the $r^{th}$ row (i.e., r=1, 2) of the $k^{th}$ column in the left half of the aperture 24 and a beamformer channel 19. $G_{rk}$ represents the interconnection between an element pair of the $r^{th}$ row (i.e., r=1, 2) of the $k^{th}$ column in the right half of the aperture and a beamformer channel.

Depending on the position of the aperture 24 along the array 40 and the aperture pattern, the switching circuit switches the appropriate element signal to the appropriate beamformer channel 19. The switching circuit 30 includes a single switch 34 for each center element signal for connecting the signal to the appropriate beamformer channel 19 identified by connectivity equation (7) below. For the off-center element pairs (i.e., r=1), other than the top row pair r=n, (r=2) three (3) switches connect the element pairs 22 to the appropriate beamformer channel 19 defined by the connectivity equation (7), equation (8) for elements pairs disposed to the left of the center 32 of the aperture 24 and equation (9) for element pairs disposed to the right of the center of the aperture. For the top row pair r=n (in this case r=2) equations (8) and (9) give identical results, therefore one switch can be eliminated leaving only two switches.

FIGS. 17A–C numerically illustrate the allocation of the beamformer channels 19 for each element 22 of the array 40 for a given zone of the imaging field 26. FIGS. 17A–C show the element to beamformer channel 19 connections in the three depth zones (Zones 1–3) when the aperture 24 is shifted by 4 positions from the left most position (as illustrated in FIGS. 6A–C), resulting in a rotation by 4 positions of the signal columns at the output of the aperture shifting circuit. FIG. 17A illustrates the aperture pattern for Zone 1. FIG. 17B illustrates the aperture for pattern Zone 2. FIG. 17C illustrates the aperture pattern for Zone 3. In both cases the beamformer channel 19 connected to each element is chosen from the available switches 34 defined for each channel by formulas (7) to (9). It can be seen that this set of switches always provides connectivity between the M element groups 22 (which vary function of the depth zone) and the M beamformer channels 19.

For example referring to FIG. 17A, the allocation of the beamformer channels 19 for the elements 22 of column 10 is determined using equations (7) and (9) because column 10 is to the right of the center 32 of the aperture 24. Using equation (7), the center element (r=0) of column 10 is connected to channel 10, where k=10. The first row of element pairs (r=1) in column 10 is connected to channel 6 in accordance to equation (9), where k=10, r=1, M=4 and M=12. The second row of element pairs (r=2) in column 10 is connected to channel 4 in accordance with equation (9), where k=10, r=2, M=4 and M=12.

The allocation of the beamformer channels 19 for the elements 22 of element column 9 is determined using equations (7) and (8) because column 9 is to the left of the center of the aperture. Using equation (7), the center element of column 9 is connected to channel 9, where k=9. The first row of element pairs (r=1) in column 9 is connected to channel 1 in accordance to equation (8), where k=9, r=1, M=4 and M=12. The second row of element pairs (r=2) in column 9 is connected to channel 3 in accordance with equation (8), where k=9, r=2, M=4 and M=12.

As shown in FIGS. 17B and 17C, the column indexes wrap around output signals of the aperture shifting circuit 42. For example, the elements in columns 8 and 9 in the right half of the aperture 24 are provided at outputs (A=0, 1) of the shifting circuit 42.

Figure 18:
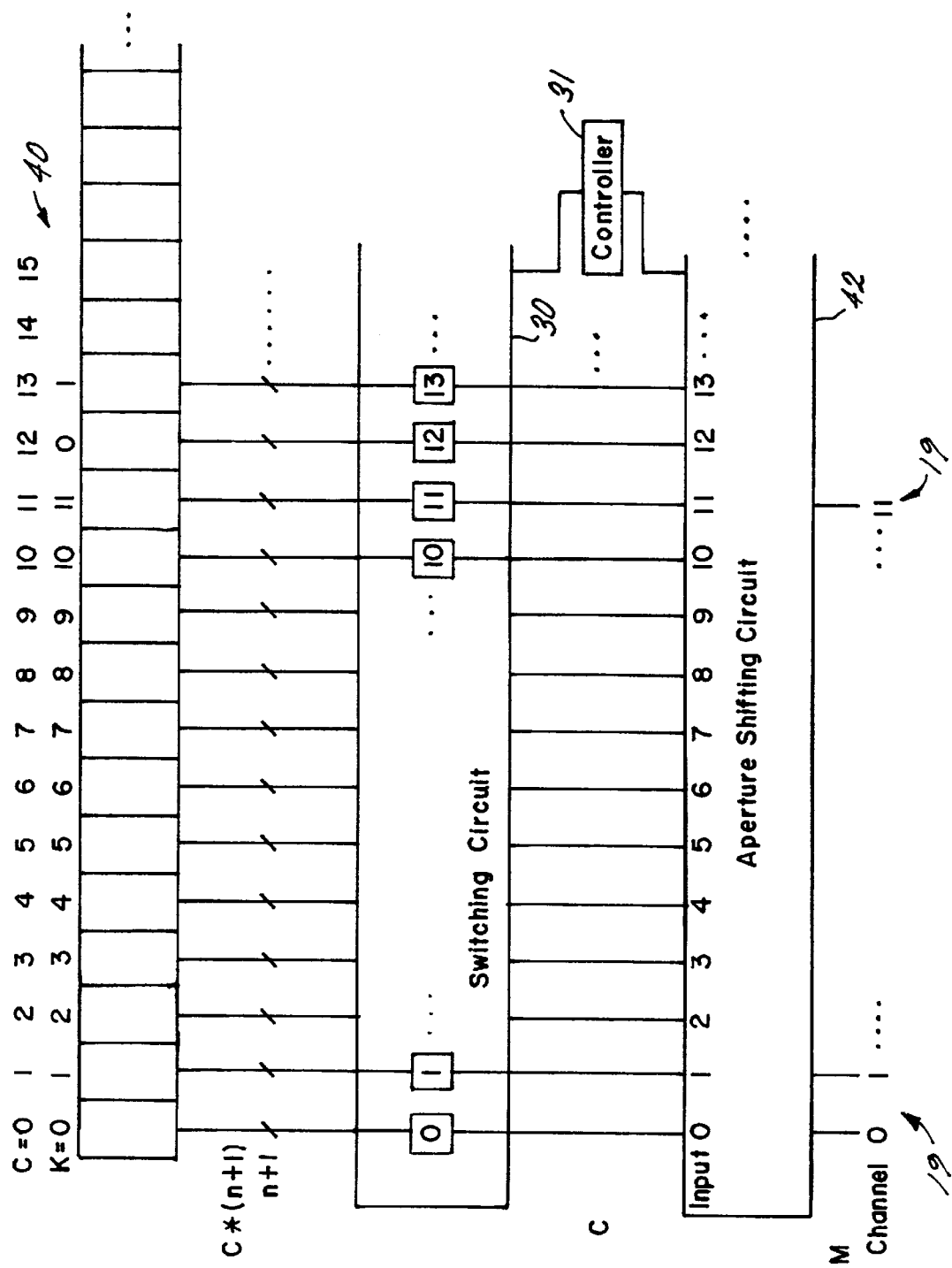
FIG. 18 shows a schematic representation of a second embodiment of an ultrasound imaging system wherein a switching circuit precedes an aperture shifting circuit.

Referring to FIG. 18, another embodiment of an array element allocation system for a linear/convex array 40 may be configured such that the switching circuit 30 precedes the aperture shifting circuit 42. The shifting circuit 42 receives all the signals provided from the linear/convex array 40 (C*[n+1] signals), with the understanding that the off-center pairs about each center element (r=0) of each column (C) are interconnected to transmit and receive a single signal. Therefore, the total number of signals provided by each column equals n+1, wherein n=the number of rows (r) of off-center pairs of elements 22. The switching circuit 30 provides C number of signals to the aperture shifting circuit 42 to activate the appropriate aperture pattern for each zone, where C=the number of columns of the array. The aperture shifting circuit 42 then connects selected column signals of the elements 22 to the beamformer channels 19 to shift the aperture 24 in the azimuth direction of the array. The aperture shifting circuit has M outputs connected to the M pairs (transmit/receive) of beamformer channels 19. The switches of the aperture shifting circuit 42 and the switching circuit 30 are actuated by a control signal provided by the controller 31 in response to a computer program.

Figure 19:
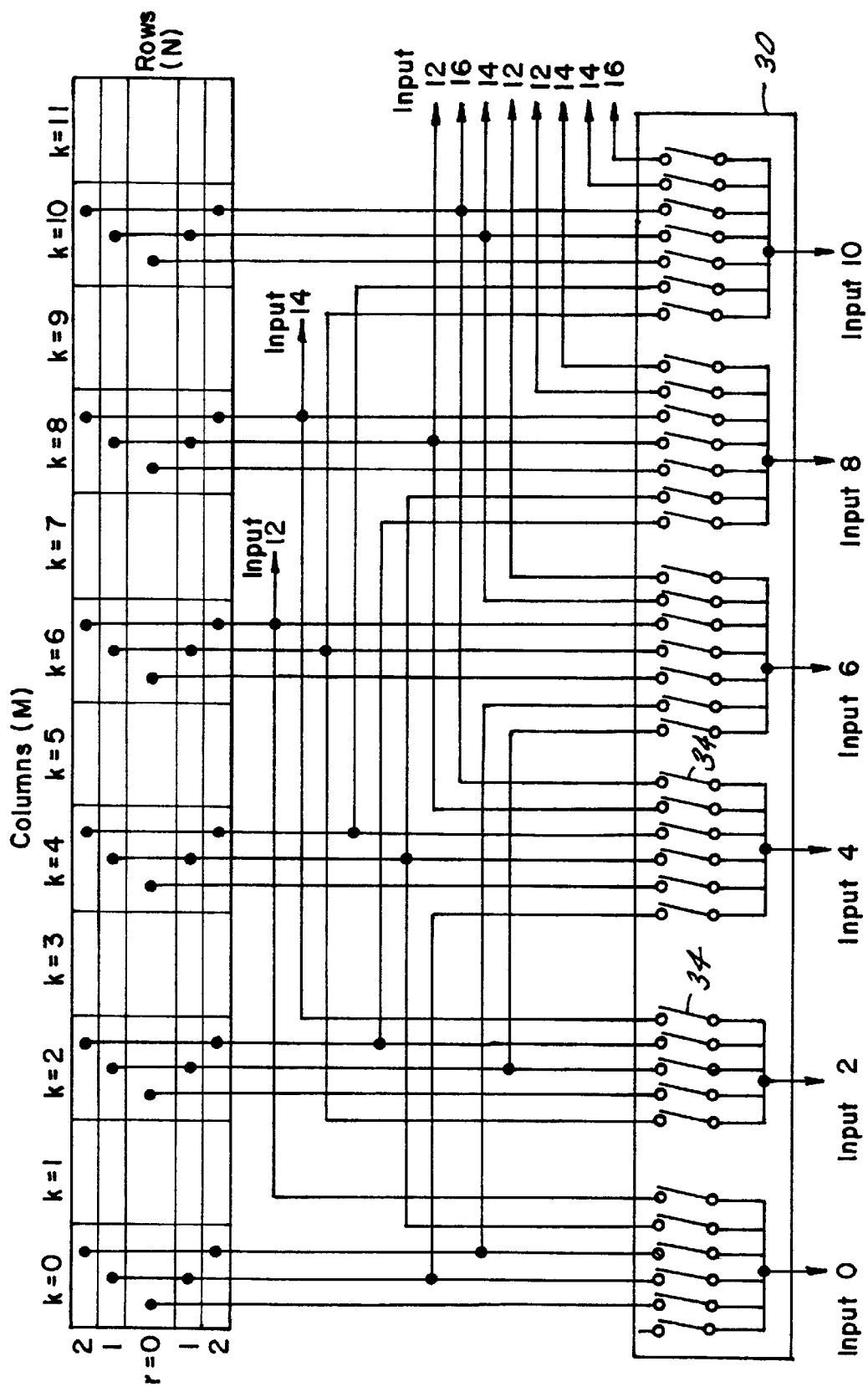
FIG. 19 shows a schematic representation of an aperture of the transducer of FIG. 18, aperture shifting circuit and switching circuit in accordance with a second allocation method.

In the second embodiment of the allocation system, as shown in FIG. 19, the switching circuit 30 provides programmable switches 34 for each element signal provided as an input to the switching circuit from the linear/convex array 40. Only a portion of the even numbered channels and corresponding switches are shown, with the understanding that the other even numbered and odd numbered channels and switches are similarly interconnected. Further, only twelve (12) columns of the total number of columns (C) of the array are shown. The following connectivity equations define the interconnection of each element signal to a corresponding beamformer channel 19:

$$E_{rk}=k \tag{10}$$

$$F_{rk}=(k+(r+1)*m/2) \tag{11}$$

$$G_{rk}=(k-(r+1)*m/2) \tag{12}$$

It should be noted that the mod M operation, as shown in equations (7)–(9), is not performed because column rotation is not necessary, as will be apparent from the discussions hereinafter. Consequently, switches $F_{rk}$ are deleted if the respective column numbers exceed C, and switches $G_{rk}$ are deleted if the respective column numbers become negative.

$E_{rk}$ represents the interconnection between a central element 22 of the $k^{th}$ column of the array 40 and an input of the aperture shifting circuit 42. $F_{rk}$ represents the interconnection between an element pair of the $r^{th}$ row (i.e., 1, 2) of the $k^{th}$ column of the array 40 when this column is in the left half of the active aperture 26 and an input of the aperture shifting circuit 42. $G_{rk}$ represents the interconnection between an element pair of the $r^{th}$ row (i.e., 1, 2) of the $k^{th}$ column of the array 40 when the column is in the right half of the active aperture and an input of the aperture shifting circuit 42.

Depending on the position of the aperture 24 along the array 40 and the aperture pattern, the switching circuit 30 switches the appropriate element signal to the aperture shifting circuit 42. The switching circuit 30 includes a single switch 34 for each center element (r=0) signal for connecting the signal to the appropriate input of the shifting circuit 42 identified by connectivity equation (10) below. For the off-center row element pairs (r=1), three (3) switches connect the pairs to the appropriate aperture shifting circuit defined by connectivity equation (10), connectivity equation (11) for element pairs disposed to the left of the center of the aperture 24, and equation (12) for element pairs disposed to the right of the center of the aperture.

The allocation of the beamformer channels 19 for each element 22 of the array 40 for a given zone of imaging field 26 that is shifted by four positions is similar to that shown in FIGS. 17A–C for the previous embodiment. For example the allocation of the input of the shifting circuit 42 for the elements of column 10 is determined using equations (10) and (11) because column 10 is to the right of the center 32 of the aperture 24. Using equation (10), the center element is connected to aperture input which is connected to channel 10, where k=10. The first row of element pairs (r=1) in column 10 is connected to aperture input which is connected to channel 10 in accordance to equation (10), where k=10, r=1, and m=4. The second row of element pairs (r=2) in column 10 is connected to aperture input which is connected to channel 4 in accordance with equation (8), where k=10, r=2, and m=4.

The allocation of the beamformer channels 19 for the elements 22 of element column 9 is determined using equations (10) and (12) because column 9 is to the left of the center 32 of the aperture 24. Using equation (10), the center element (r=0) is connected to aperture input which is connected to channel 9, where k=9. The first row of element pairs (r=1) in column 9 is connected to aperture input which is connected to channel 13 in accordance with equation (12), where k=9, r=1 and m=4. The second row of element pairs (r=2) in column 9 is connected to the aperture input connected to channel 15 in accordance with equation (12), where k=9, r=2 and m=4.

Figure 20:
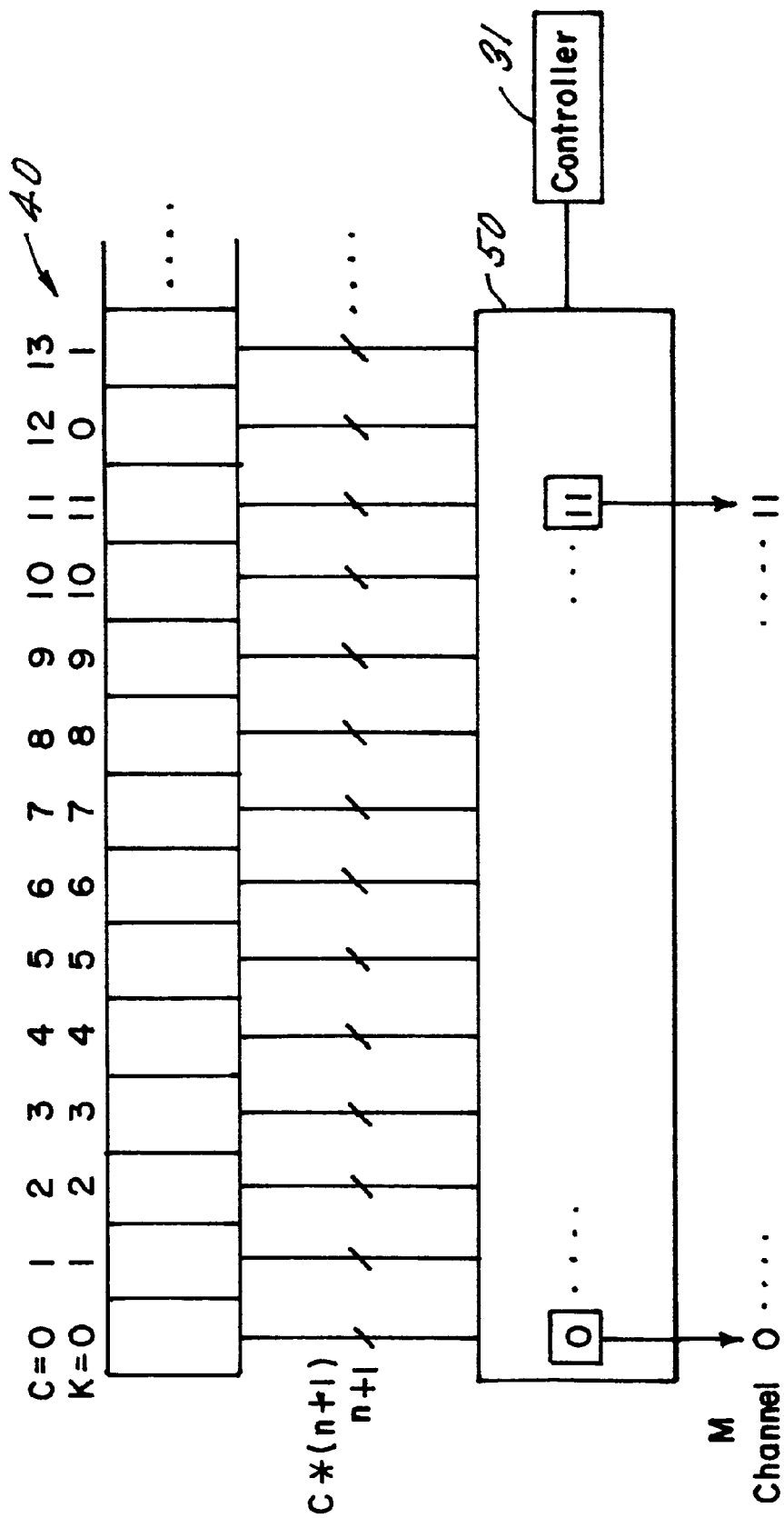
FIG. 20 shows a schematic representation of a third embodiment of an ultrasound imaging system having a combined switching circuit and aperture shifting circuit.

Referring to FIG. 20, another embodiment of an array element allocation system for a linear/convex array 40 may be configured such that the switching circuit 30 and the aperture shifting circuit 42 of FIGS. 16 and 18 are integrated into a combined switching circuit 50. The combined switching circuit 50 receives all the signals provided from the linear array 40 (C*[n+1] signals), with the understanding that the off-center pairs(r=1, 2) about each center element 22 (r=0) of each column (C) are interconnected to transmit and receive a single signal. Therefore, the total number of signals provided by each column (C) equals n+1, wherein n=the number of rows of off-center pairs of elements 22. The combined switching circuit 50 provides M signals to the respective beamformer channels 19, where m=the number of beamformer channels. The combined switching circuit 50 provides both function of switching the connections from the beamformer channels 19 and the elements 22 of the array 40 and the function of shifting the aperture 24 in the azimuth direction of the array. The combined switching circuit 50 has M outputs connected to the M pairs (transmit/receive) of beamformer channels 19. The switches of the combined switching circuit 50 are actuated by a control signal provided by the controller 31 in response to a computer program.

The following connectivity equations define the interconnection of each element 22 to a corresponding beamformer channel 12:

$$E_{rk} = k \bmod M \tag{13}$$

$$F_{rk} = (k + (r+1)*m/2) \bmod M \tag{14}$$

$$G_{rk} = (M + k - (r+1)*m/d2) \bmod M \tag{15}$$

$E_{rk}$ represents the interconnection between a central element r=0 of the $k^{th}$ column of the array 40 and a beamformer channel 19. $F_{rk}$ represents the interconnection between an element pair of the $r^{th}$ row (r=1, 2) of the $k^{th}$ column in the left half of the aperture 24 and a beamformer channel 19. $G_{rk}$ represents the interconnection between an element pair of the $r^{th}$ row (r=1, 2) of the $k^{th}$ column in the right half of the aperture 24 and a beamformer channel 19.

Depending on the position of the aperture 24 along the array 40 and the aperture pattern, the combined switching circuit 50 switches the appropriate element 22 to the beamformer channel 19. The combined switching circuit 50 includes a single switch for each center element signal for connecting the signal to the appropriate beamformer channel identified by connectivity equation (13) below. For the off-center row element pairs other than the top row pair r=n, three (3) switches connect the pairs to the appropriate aperture input defined by connectivity equation (14) for element pairs disposed to the left of the center of the aperture and connectivity equation (15) for element pairs disposed to the right of the center of the aperture. For the top row pair r=n equations (14) and (15) give identical results, therefore one of the switches can be eliminated leaving only two switches.

The allocation of the beamformer channels 19 for each element 22 of the array 40 for a given zone of the imaging field 26 that is shifted by four positions is similar to that shown in FIGS. 17A–C for the previous embodiment. For example, the allocation of the input of the combined circuit 50 for the elements 22 of column 10 is determined using equations (13) and (15) because column 10 is to the right of the center 23 of the aperture 24. Using equation (13), the center element (r=0) is connected to beamformer channel 10, where k=10. The first row of element pairs (r=1, 2) in column 10 is connected to channel 6 in accordance to equation (15), where k=10, r=1, and m=4. The second row of element pairs (r=2) in column 10 is connected to channel 4 in accordance with equation (14), where k=10, r=2, and m=4.

The allocation of the beamformer channels 19 for the elements 22 of element column 9 is determined using equations (13) and (14) because column 9 is to the left of the center 32 of the aperture 24. Using equation (13), the center element is connected to beamformer channel 9, where k=9. The first row of element pairs (r=1) in column 9 is connected to channel 13 in accordance to equation (14), where k=9, r=1 and m=4. The second row of element pairs (r=2) in column 9 is connected to channel 15 in accordance with equation (14), where k=9, r=2 and m=4.

Figure 21:
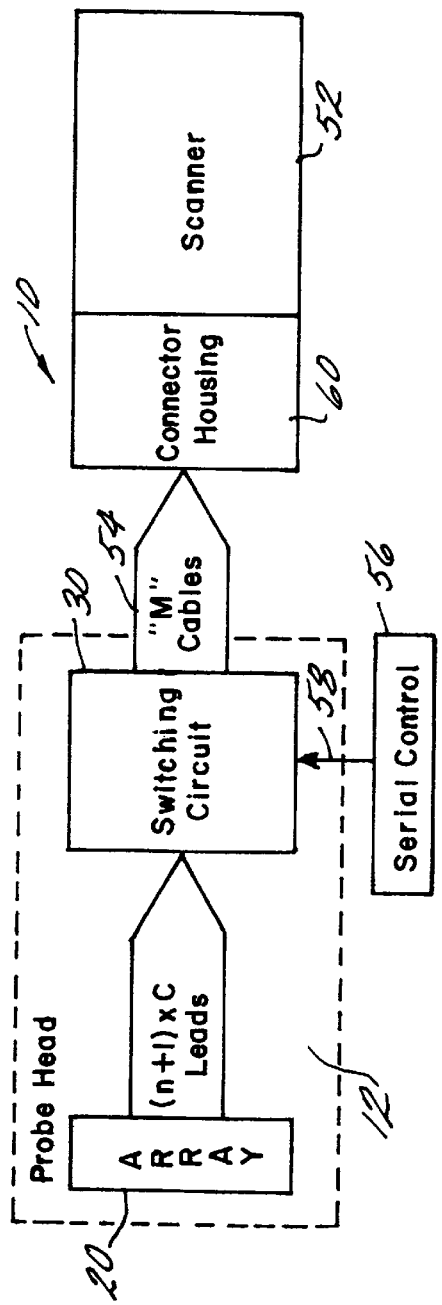
FIG. 21 shows a block diagram of an embodiment of an ultrasonic imaging system.
Figure 22:
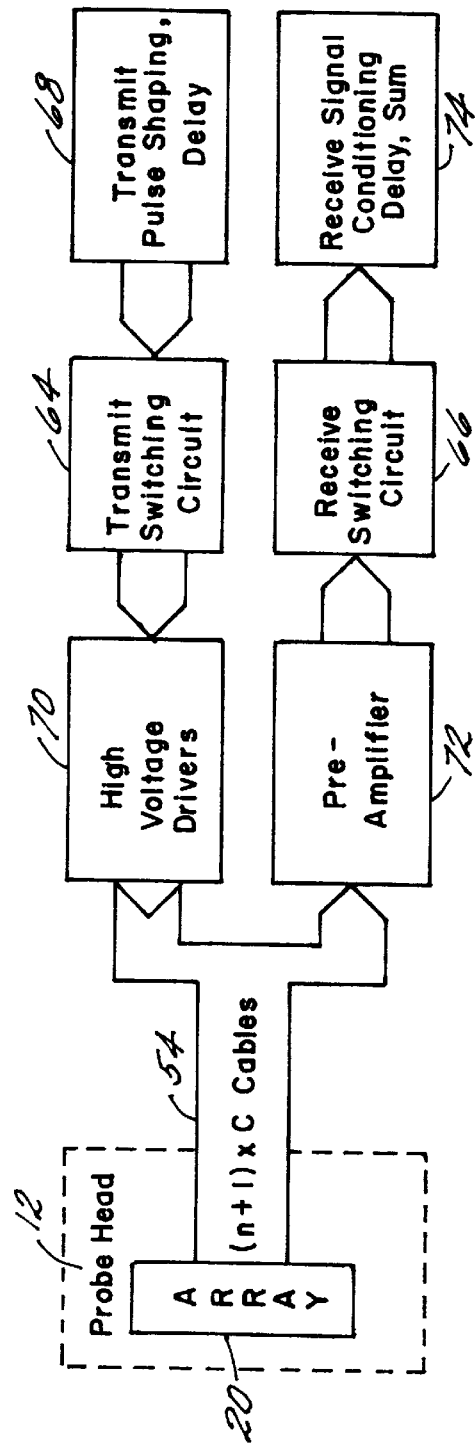
FIG. 22 shows a block diagram of a second embodiment of an ultrasonic imaging system.

Referring to FIG. 21, the switching circuit 30 for a phased array probe head (as shown in FIG. 5) or a convex/linear array probe head 12 (as shown in FIGS. 14, 16 and 18) may be disposed between the elements 22 of the array 20 and the transmit/receive circuits (not shown) of the scanner 52. In this embodiment, the switching circuit 30 is preferably mounted within the probe head 12, such that the number of cables between the probe head 12 and the scanner is equal to the number of beamformer channels M. It should be noted that the ultrasound cable 54 also includes a serial control 56 for controlling the switches of the switching circuit 30. The number of control lines 58 may be kept small by using integrated switch circuits with built-in control latches (such as a SUPERTEX HV202) and control line multiplexing. An advantage of this embodiment is that the existing imaging systems 10 may be adapted for elevation focusing according to the present invention with minimal changes to the scanner 52.

Alternatively, the switching circuit 30 array may be disposed in the probe's connector housing 60 to reduce the size of the probe head 12 of the previous embodiment. While the number of cables 54, 58 is increased from approximately M cables to C*(n+1) cables, the number of connector pins (not shown) is minimized to M pins which allows adapting probes 12 with elevation focusing to the existing systems with minimal changes to the scanner.

These approaches are advantageous in reducing the number of cables 54, 58 and/or connector pins to minimize the system cost when most of the probes 12 used with the scanner 52 are of the traditional type, with a single row of elements 22. If many of the probes are expected to have multiple rows of elements for elevation focusing, then it may be more economical to build the switching circuit 30 into the front-end of the scanner 52 as is commonly done with the aperture shifting circuit 42.

In the alternative to the above approach of disposing the switching circuit 30 between the array 20 and the high voltage transmit/receive circuits 62 of the scanner 52 as shown in FIG. 21, separate switching circuits 64, 66 may be provided for the transmit and receive beamformers. The transmit switching circuit 64 is disposed between the transmit signal generators 68 and high-voltage drivers 70. The receive switching circuit 66 is disposed between the receive pre-amplifiers 72 and the receive signal conditioning and beamforming. 74. One skilled in the art would appreciate that it is also possible to place the receive switching circuit 66 before the receive preamplifiers 72, thus reducing the number of preamplifiers 72 but sacrificing to some extent the signal to noise ratio performance.

Figure 23:
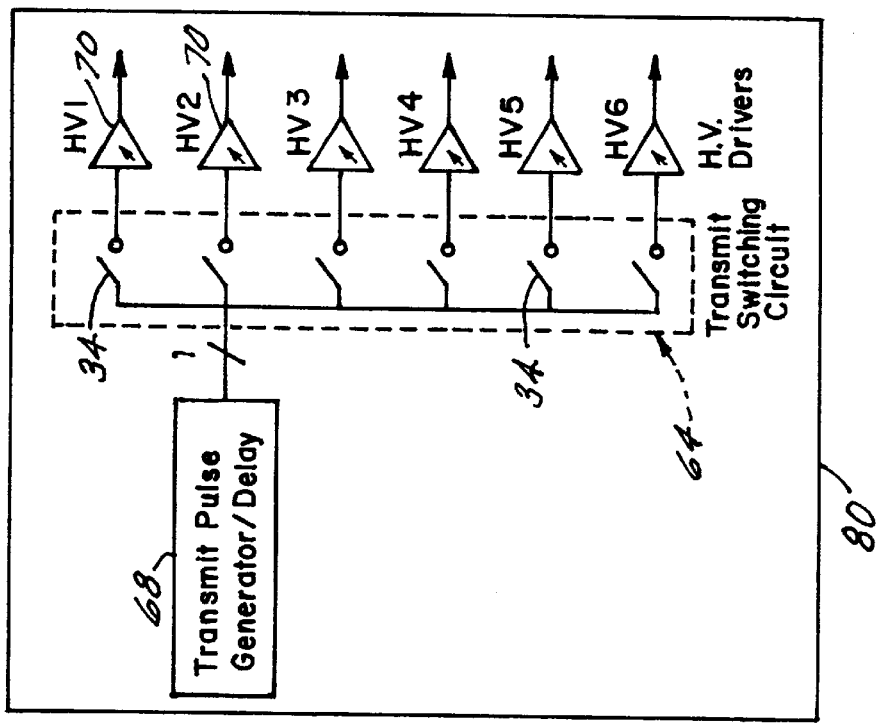
FIG. 23 shows a schematic diagram of a transmitter of a beamformer channel of a transducer employing the present invention.

FIG. 23 shows one channel of the transmit switching circuit 80, connected in this example to six (6) element pairs. A transmitter generator 68 is connected to the switches 34 of the transmit switching circuit 64. Each switch 34 is connected to a respective high voltage driver HV1 to HV6 (70). The switches may comprise FET transistors or logic gates. The output amplitude of the high voltage drivers 70 are controlled for transmit apodization by independently controlling the high voltage power supplies feeding the different groups of drivers. Control of the high voltage power supply may be achieved by adjusting the gain of the drivers 70 or by adjusting the amplitude of the signals provided to the drivers' inputs.

Figure 24:
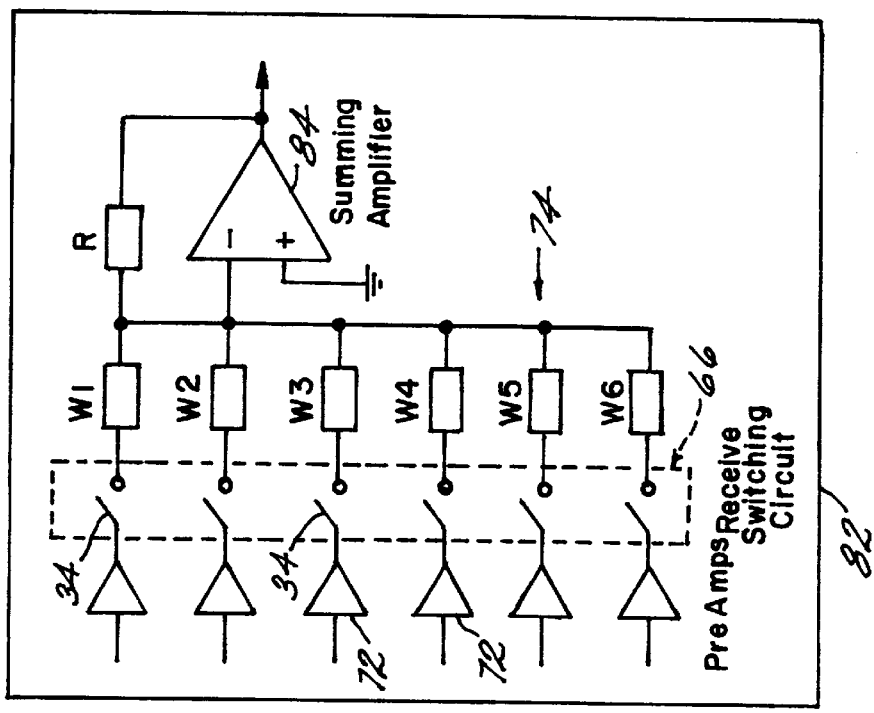
FIG. 24 shows a schematic diagram of a receiver of a beamformer channel of a transducer employing the present invention.

FIG. 24 shows one channel of the receive switching circuit 66, connected to 6 element pairs. Each of the six element pairs is connected to a pre-amplifier 72 which is connected to a switch 34 of the receive switching circuit 66. The switches of the receive switching circuit may consist of FET transistors or current switches. The receive switching circuit 66 is connected to a summing circuit 74 including a summing amplifier 84 and resistors W1–W6 and R, however, it will be appreciated that current summers may also be used. The summing circuit 74 has different (preferably programmable) weights for the different elements, allowing receive apodization.

This arrangement relaxes the requirements on the switch technology concerning the size and power dissipation of the embodiments of FIG. 21 because there is much more room and cooling capability in the system console than in the probe 12. In addition, the switches 34 do not operate at high voltage, and the element loading is reduced. In other words, each element 22 of the array 20 is connected to one cable, one driver and one receiver. Transmit and receive apodization is also easier to implement, and therefore improves focusing capability of the imaging system.

It will be appreciated that the choice of aperture size described by equations (1) and (2), the associated (n+1) zone scheme with azimuthal expansion in increments of m, and the respective switching circuits 30 as described hereinbefore are preferred from the standpoint of clarity of explanation. One will, therefore, appreciate that alternative aperture configurations and zone sequences realizing different operational, performance and cost objectives may be designed, in accordance with the present invention.

For example, it may be advantageous for the aperture 24 in Zone 1 to have an ellipsoidal pattern instead of a rectangular one. In addition, more beamformer channels 19 may be allocated to the azimuthal center-row elements 22 and less beamformer channels to elevational elements (r=1, 2). In this case each row pair (r=1, 2) may start out with a different number of elements 22 such that: $M_0+M_1+\ldots M_n=M$ (number of beamformer channels). The switching circuits 30 for this configuration are built based on the same principles as discussed in hereinbefore, but the terms of the form (r+1)*m/2 in the equations (3) to (15) are replaced by sums of the form:

$$M_0+(M_1+\ldots M_{r-1})/2 \qquad (16)$$

It is also possible to reduce the size of the switching circuit 30 by using hybrid configurations where some of the array elements 22 are switched according to the method of the invention while other elements are not switched. For example, if a scanner has the typical 128 beamformer channels 19 but the probe's geometry produces best results with a smaller (e.g. 64 elements) azimuthal aperture, as is the case with certain convex probes 12 in which the element directivity and the probe's curvature restrict the useful azimuthal aperture size, then some rows may be switched according to the method of the invention using for example 64 channels, while other rows (with a total number of 64 elements in the aperture) may be used in the conventional manner. It is also possible to apply the method of the invention only up to a row pair j (where j<n), and to use only aperture control, not independent beamformer delays for the row pairs j+1 to n.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. An imaging system for focusing ultrasound beams in elevational and azimuthal planes; the system comprising:

an array having a plurality of rows of imaging elements in an elevational direction and a plurality of columns of imaging elements in an azimuthal direction;

a plurality of beamformer channels, each beamformer channel including a transmit beamformer and a receive beamformer;

a switching circuit, including a plurality of switches, that allocates, in response to a control signal, at least one beamformer channel to an elevational element of a first aperture having a predetermined number of columns and rows for scanning a first depth of an imaging field, and to an azimuthal element of a column added to the first aperture to form a second aperture for scanning a second depth of the imaging field;

a controller providing a control signal for allocating the at least one beamformer channel between the elevational element and the azimuthal element of the array.

2. The imaging system, as defined in claim 1, wherein the first depth of the imaging field is closer to the array than the depth of the second depth.

3. The imaging system, as defined in claim 2, wherein the first aperture is rectangular in shape.

4. The imaging system, as defined in claim 2, wherein the first aperture is elliptical in shape.

5. The imaging system, as defined in claim 1, wherein the array has an odd number of rows comprising a center row of elements and at least a first pair of symmetrical rows of elements disposed about the center row.

6. The imaging system, as defined in claim 5, wherein the elements of the first pair of symmetrical rows of each column are interconnected.

7. The imaging system, as defined in claim 5, wherein the elements of the first pair of symmetrical rows have height different than height of the elements of the center row.

8. The imaging system, as defined in claim 7, wherein the elements of the center row have a height greater than a height of the elements of the first pair of symmetrical rows.

9. The imaging system, as defined in claim 1, wherein the array further includes a second pair of symmetrical rows of elements disposed about the center row, wherein the elements of the second pair of symmetrical rows of each column are interconnected.

10. The imaging system, as defined in claim 9, wherein the elements between the first pair and second pair of symmetrical rows are different.

11. The imaging system, as defined in claim 5, wherein the elevational element is disposed in a symmetrical row and is adjacent an element of the center row of the first aperture and the azimuthal element is an element of the center row of the column added to the first aperture.

12. The imaging system, as defined in claim 11, wherein the switching circuit further allocates the elevational element to the beamformer channel allocated to the central element of the column of the elevational element.

13. The imaging system, as defined in claim 5, wherein the central elements of the columns of the first aperture are directly connected to a corresponding beamformer channel.

14. The imaging system, as defined in claim 5, wherein elements of the center row and elements of adjacent symmetrical rows are hardwired together in accordance with a predetermined aperture.

15. The imaging system, as defined in claim 1, wherein a predetermined number of elements are open to a beamformer channel in accordance with the aperture pattern.

16. The imaging system, as defined in claim 1, wherein the switching circuit allocates beamformer channels between a plurality of respective elevational elements of the first aperture and a plurality of respective elements of added columns symmetrically disposed on each side of the first aperture to form the second aperture.

17. The imaging system, as defined in claim 1, wherein the switching circuit allocates at least one beamformer channel to both the elevational element of the first aperture and an adjacent element in the same column of the elevational element.

18. The imaging system, as defined in claim 1, wherein the azimuthal element of the added column is added to the first aperture on the side opposite the elevational element relative to a center of the first aperture.

19. The imaging system, as defined in claim 18, wherein each azimuthal element of a plurality of added columns are added to the side of the first aperture pattern opposite the elevational elements, wherein the order of adding the added columns to the first aperture is relative to the position of the elevational elements to the center of the first aperture.

20. The imaging system, as defined in claim 19, wherein the beamformer channel allocated to the reallocated element closest to the center of the first aperture is allocated to the azimuthal element of the column adjacent the first aperture.

21. The imaging system, as defined in claim 19, wherein the beamformer channel allocated to the elevational element furthest from the center of the first aperture is allocated to the element of the column adjacent the first aperture.

22. The imaging system, as defined in claim 1, wherein the azimuthal element of the added column is added to the first aperture on the same side as the element relative to a center of the first aperture.

23. The imaging system, as defined in claim 22, wherein each azimuthal element of a plurality of added columns are added to the side of the first aperture pattern on the same side as the elevational elements, wherein the order of adding the added columns to the first aperture is relative to the position of the elevational elements to the center of the first aperture.

24. The imaging system, as defined in claim 23, wherein the beamformer channel allocated to the elevational element closest to the center of the first aperture is allocated to the element of the column adjacent the first aperture.

25. The imaging system, as defined in claim 23, wherein the beamformer channel allocated to the elevational element furthest from the center of the first aperture is allocated to the element of the column adjacent the first aperture.

26. The imaging system, as defined in claim 1, further includes a mechanical lens for focusing the ultrasound beams in the elevational plane in a furthest depth of an imaging field.

27. The imaging system, as defined in claim 1, wherein the array is a phased array.

28. The imaging system, as defined in claim 1, wherein the array is a linear array.

29. The imaging system, as defined in claim 1, wherein the array is a curvilinear array.

30. The imaging system, as defined in claim 1, further comprising:
    an aperture shifting circuit, including a plurality of switches, that allocates, in response to a control signal, the beamformer channels to the elements of the array to shift the active aperture of the array along the azimuthal direction, wherein the controller provides a control signal for shifting the elements of the aperture along the array in accordance with a computer program.

31. The imaging system, as defined in claim 1, further comprising:
    an aperture shifting circuit, including a plurality of switches, that allocates, in response to a control signal, the beamformer channels allocated to the elements of the column adjacent one end of the active aperture to the elements of the column adjacent the other end of the active aperture to shift the active aperture along the array in the azimuthal plane, wherein the controller provides a control signal for shifting the elements of the aperture along the array in accordance with a computer program.

32. The imaging system, as defined in claim 1, wherein the aperture shifting circuit is connected to the beamformer channels and the switching circuit, and the switching circuit is connected to the array.

33. The imaging system, as defined in claim 1, wherein the switching circuit is connected to the beamformer channels and the aperture shifting circuit, and the aperture shifting circuit is connected to the array.

34. The imaging system, as defined in claim 1, wherein the switching circuit further allocates, in response to the control signal, the beamformer channels allocated to the elements of the column adjacent one end of the active aperture to the elements of the column adjacent the other end of the active aperture to shift the active aperture along the array in the azimuthal plane, wherein the controller provides a control signal for shifting the elements of the aperture along the array in accordance with a computer program.

35. The imaging system, as defined in claim 1, wherein the switching circuit is connected to the array, and the switching circuit and the array are disposed within a head portion of a probe.

36. The imaging system, as defined in claim 1, wherein the switching circuit is connected to the array, and the switching circuit is disposed within a connector housing of a probe.

37. The imaging system, as defined in claim 9, wherein less than all the beamformer channels are allocated to an aperture.

38. The imaging system, as defined in claim 9, wherein the switching circuit allocates less than all the symmetrical rows of elements.

39. An imaging system for focusing ultrasound beams in elevational and azimuthal planes; the system comprising:

an array having a plurality of rows of imaging elements in an elevational direction and a plurality of columns of imaging elements in an azimuthal direction;

a plurality of transmit beamformer channels including a transmit switching circuit, having a plurality of switches, that allocates, in response to a control signal, at least one transmit beamformer channel to an elevational element of a first aperture having a predetermined number of columns and rows for scanning a first depth of an imaging field, and to an azimuthal element of a column added to the first aperture to form a second aperture for scanning a second depth of the imaging field;

a plurality of receive beamformer channels including a receive switching circuit, having a plurality of switches, that allocates, in response to a control signal, at least one receive beamformer channel to an elevational element of a first aperture having a predetermined number of columns and rows for scanning a first depth of an imaging field, and to an azimuthal element of a column added to the first aperture to form a second aperture for scanning a second depth of the imaging field; and a controller providing a control signals for allocating the at least one transmit beamformer channel and at least one receive beamformer channel between the elevational element and the azimuthal element of the array.

40. A method for focusing ultrasound beams for an array having a plurality of rows of imaging elements in an elevational direction and a plurality of columns of imaging elements in an azimuthal direction; said method comprising:

allocating each of a plurality of beamformer channels to elevational and azimuthal elements defining a first aperture having a predetermined number of rows and columns of elements for scanning a first depth of an imaging field;

focusing an ultrasound beam in the elevational and azimuthal planes at the first depth of the imaging field;

reallocating at least one beamformer channel of an elevational element of the first aperture to at least one azimuthal element of an added column to form a second aperture for scanning a second depth of the imaging field; and focusing an ultrasound beam in the elevational direction and azimuthal direction at the second depth of the imaging field.

41. The method, as defined in claim 40, wherein adding at least one column further comprises allocating a corresponding number of beamformer channels from elevational elements of the first aperture pattern to respective azimuthal elements of added columns to form the second aperture, wherein the added columns are added symmetrically to each side of the first aperture.

42. The method, as defined in claim 40, further comprising:

allocating at least one beamformer channel of an element of the first aperture to the elevational element of the first aperture.

43. The method, as defined in claim 40, wherein the array has an odd number of rows comprising a center row of elements and at least a first pair of symmetrical rows of elements disposed about the center row.

44. The method, as defined in claim 43, wherein elements of the first pair of symmetrical rows are interconnected.

45. The method, as defined in claim 43, wherein the element of the first pair of symmetrical rows have height different than height of the elements of the center row.

46. The method, as defined in claim 45, wherein the elements of the center row have a height greater than a height of the elements of the first pair of symmetrical rows.

47. The method, as defined in claim 43, wherein allocating at least one beamformer channel comprises:

allocating the at least one beamformer channel from an elevational element of a row adjacent the center row of the first aperture to an element of the center row of the column added to the first aperture; and allocating a beamformer channel of a central element of the column of the elevational element to the elevational element.

48. The method, as defined in claim 40, wherein the at least one azimuthal element of the added column is added to the first aperture on the side opposite the elevational element relative to a center of the first aperture.

49. The method, as defined in claim 48, wherein the at least one azimuthal element of the added column is adjacent the side of the first aperture opposite the elevational element closest to the center of the first aperture.

50. The method, as defined in claim 48, wherein the at least one azimuthal element of the added column is adjacent the side of the first aperture opposite the elevational element furthest from the center of the first aperture.

51. The method, as defined in claim 40, wherein the at least one azimuthal element of the added column is added to the first aperture on the same side of the elevational element relative to a center of the first aperture.

52. The method, as defined in claim 51, wherein the at least one azimuthal element of the added column adjacent the same side of the first aperture as the elevational element closest to the center of the first aperture.

53. The method, as defined in claim 51, wherein the at least one azimuthal element of the added column is adjacent the same side of the first aperture as the elevational element furthest from the center of the first aperture.

54. The method, as defined in claim 40, wherein the array is a phase array.

55. The method, as defined in claim 40, wherein the array is a linear array.

56. The method, as defined in claim 40, wherein the array is a curvilinear array.

57. The method, as defined in claim 43, wherein the central elements of the first aperture are directly connected to the beamformer channel.

58. The method, as defined in claim 43, wherein the elements of the center row and adjacent rows are hardwired together in accordance with the aperture pattern.

59. The method, as defined in claim 40, wherein of a predetermined number of elements are open to a beamformer channel in accordance with the aperture pattern.

60. The method, as defined in claim 55, further comprising:

allocating the elements of the first aperture to shift the aperture along the azimuthal plane of the array.

61. The method, as defined in claim 40, further comprising:

determining the columns of the active aperture; and allocating the beamformer channels to the elements of the active aperture in accordance with a desired aperture pattern and position of the active aperture on the array.

* * * * *